(12) United States Patent
Quadri et al.

(10) Patent No.: US 8,337,541 B2
(45) Date of Patent: Dec. 25, 2012

(54) DELIVERY SYSTEM FOR VASCULAR IMPLANT

(75) Inventors: Arshad Quadri, West Hartford, CT (US); J. Brent Ratz, Winchester, MA (US)

(73) Assignee: CardiAQ Valve Technologies, Inc., Irvine, CA (US)

( * ) Notice: Subject to any disclaimer, the term of this patent is extended or adjusted under 35 U.S.C. 154(b) by 528 days.

(21) Appl. No.: 12/572,180

(22) Filed: Oct. 1, 2009

(65) Prior Publication Data

US 2010/0082089 A1 Apr. 1, 2010

Related U.S. Application Data

(60) Provisional application No. 61/136,760, filed on Oct. 1, 2008.

(51) Int. Cl.
*A61F 2/84* (2006.01)
(52) U.S. Cl. .................................... 623/1.11
(58) Field of Classification Search ......... 623/1.11–1.54
See application file for complete search history.

(56) References Cited

U.S. PATENT DOCUMENTS

| | | | |
|---|---|---|---|
| 5,397,355 A | 3/1995 | Marin | |
| 5,411,552 A | 5/1995 | Anderson et al. | |
| 5,439,446 A * | 8/1995 | Barry | 604/103.01 |
| 5,474,563 A | 12/1995 | Myler et al. | |
| 5,807,398 A * | 9/1998 | Shaknovich | 623/1.11 |
| 5,855,601 A | 1/1999 | Bessler et al. | |
| 5,879,381 A | 3/1999 | Moriuch et al. | |
| 5,935,108 A | 8/1999 | Katoh | |
| 6,004,328 A | 12/1999 | Solar | |
| 6,053,940 A | 4/2000 | Wijay | |
| 6,113,612 A | 9/2000 | Swanson et al. | |
| 6,159,237 A | 12/2000 | Alt | |
| 6,168,616 B1 * | 1/2001 | Brown, III | 623/1.11 |
| 6,251,093 B1 | 6/2001 | Valley et al. | |
| 6,425,916 B1 | 7/2002 | Garrison et al. | |

(Continued)

FOREIGN PATENT DOCUMENTS

GB 2245495 1/1992

(Continued)

OTHER PUBLICATIONS

PCT; International Search Report for PCT/US2009/059299; Dec. 18, 2009.

(Continued)

*Primary Examiner* — David Isabella
*Assistant Examiner* — Ann Schillinger
(74) *Attorney, Agent, or Firm* — Knobbe Martens Olson & Bear LLP

(57) ABSTRACT

A medical treatment system and method of treatment is described having an implant that can be positioned and deployed, then undeployed to allow repositioning of the implant. The system includes a self-expanding medical implant that longitudinally foreshortens upon radially expanding from a radially compacted state, a distal interface configured to attach the implant to a distal mount of a delivery device, and a proximal interface configured to attach the implant to a proximal mount of the delivery device. Moving the distal mount longitudinally away from the proximal mount applies a longitudinal tension to the implant causing the implant to expand longitudinally and contract radially, and moving the distal mount toward the proximal mount reduces a longitudinal tension in the implant allowing the implant to expand radially toward a fully expanded state.

14 Claims, 20 Drawing Sheets

U.S. PATENT DOCUMENTS

| | | |
|---|---|---|
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock |
| 6,676,698 B2 | 1/2004 | McGuckin et al. |
| 6,767,362 B2 | 7/2004 | Schreck |
| 6,830,584 B1 | 12/2004 | Seguin |
| 6,979,350 B2 | 12/2005 | Moll et al. |
| 7,018,406 B2 | 3/2006 | Seguin et al. |
| 7,186,265 B2 | 3/2007 | Sharkawy et al. |
| 7,201,772 B2 | 4/2007 | Schwammenthal et al. |
| 7,329,278 B2 | 2/2008 | Seguin et al. |
| 7,381,219 B2 | 6/2008 | Salahieh et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,585,321 B2 | 9/2009 | Cribier |
| 2002/0045929 A1* | 4/2002 | Diaz .......................... 623/1.11 |
| 2002/0111647 A1 | 8/2002 | Khairkhahan et al. |
| 2003/0220683 A1 | 11/2003 | Minasian et al. |
| 2004/0039436 A1 | 2/2004 | Spenser et al. |
| 2004/0210304 A1 | 10/2004 | Seguin et al. |
| 2005/0090887 A1 | 4/2005 | Pryor |
| 2005/0096738 A1 | 5/2005 | Cali et al. |
| 2005/0137682 A1 | 6/2005 | Justino |
| 2005/0137690 A1 | 6/2005 | Salahieh et al. |
| 2005/0137695 A1 | 6/2005 | Salahieh et al. |
| 2005/0137701 A1 | 6/2005 | Salahieh et al. |
| 2005/0182483 A1 | 8/2005 | Osborne et al. |
| 2005/0234546 A1 | 10/2005 | Nugent et al. |
| 2005/0283231 A1 | 12/2005 | Haug et al. |
| 2006/0195183 A1 | 8/2006 | Navia et al. |
| 2007/0010876 A1 | 1/2007 | Salaheih et al. |
| 2007/0043435 A1 | 2/2007 | Seguin et al. |
| 2007/0118206 A1 | 5/2007 | Colgan et al. |
| 2007/0118207 A1 | 5/2007 | Amplatz et al. |
| 2007/0162107 A1 | 7/2007 | Salahieh et al. |
| 2007/0185559 A1 | 8/2007 | Shelso |
| 2007/0213813 A1 | 9/2007 | Von Segesser et al. |
| 2007/0250151 A1 | 10/2007 | Pereira |
| 2007/0255391 A1 | 11/2007 | Hojeibane et al. |
| 2007/0270932 A1 | 11/2007 | Headley et al. |
| 2008/0009934 A1 | 1/2008 | Schneider et al. |
| 2008/0071363 A1 | 3/2008 | Tuval et al. |
| 2008/0125859 A1 | 5/2008 | Salahieh et al. |
| 2008/0133003 A1 | 6/2008 | Seguin |
| 2008/0140189 A1 | 6/2008 | Nguyen et al. |
| 2008/0208328 A1 | 8/2008 | Antocci et al. |
| 2008/0221672 A1 | 9/2008 | Lamphere et al. |
| 2008/0243245 A1 | 10/2008 | Thambar et al. |
| 2008/0269878 A1 | 10/2008 | Iobbi |
| 2009/0005863 A1 | 1/2009 | Goetz et al. |
| 2009/0076598 A1 | 3/2009 | Salahieh et al. |
| 2009/0132035 A1 | 5/2009 | Roth et al. |
| 2009/0138079 A1 | 5/2009 | Tuval et al. |
| 2009/0163934 A1 | 6/2009 | Raschdorf et al. |
| 2009/0216314 A1 | 8/2009 | Quadri |
| 2009/0248132 A1 | 10/2009 | Bloom et al. |
| 2009/0248133 A1 | 10/2009 | Bloom et al. |
| 2009/0264997 A1 | 10/2009 | Salaheih et al. |
| 2009/0276040 A1 | 11/2009 | Rowe et al. |
| 2009/0287299 A1 | 11/2009 | Tabor et al. |
| 2009/0306768 A1 | 12/2009 | Quadri |
| 2010/0036479 A1 | 2/2010 | Hill et al. |
| 2010/0082094 A1 | 4/2010 | Quadri et al. |
| 2010/0298931 A1 | 11/2010 | Quadri et al. |
| 2011/0022157 A1 | 1/2011 | Essinger et al. |
| 2011/0022165 A1 | 1/2011 | Oba et al. |

FOREIGN PATENT DOCUMENTS

| | | |
|---|---|---|
| WO | WO 01/35870 | 5/2001 |
| WO | WO 03/092554 | 11/2003 |
| WO | WO 2005/011534 | 2/2005 |
| WO | WO 2005/087140 | 9/2005 |
| WO | WO 2007/123658 | 11/2007 |
| WO | WO 2008/091515 | 7/2008 |

OTHER PUBLICATIONS

International Search Report and Written Opinion for PCT/US2010/031313, mailed Dec. 22, 2010.

* cited by examiner

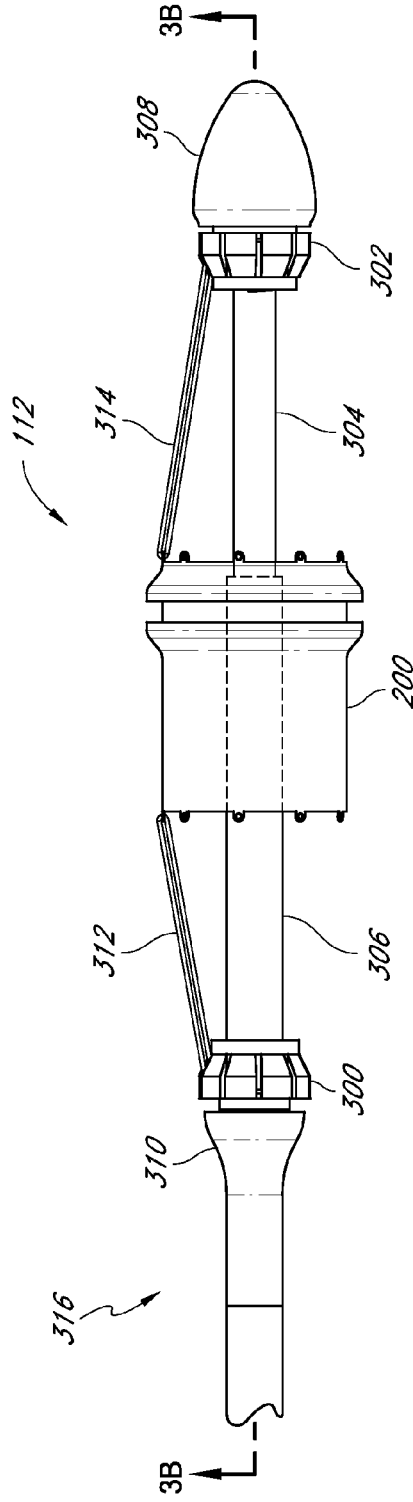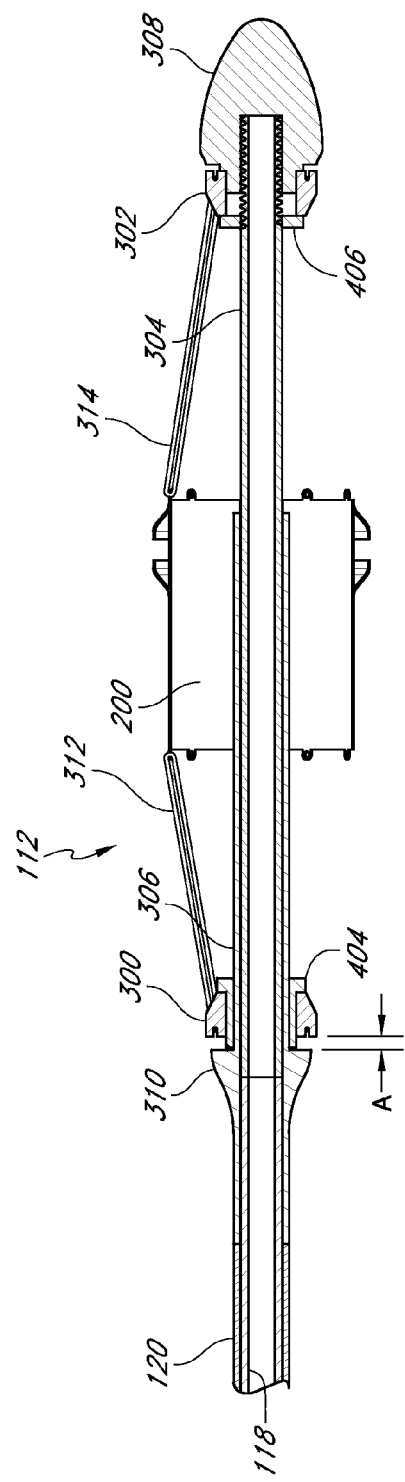

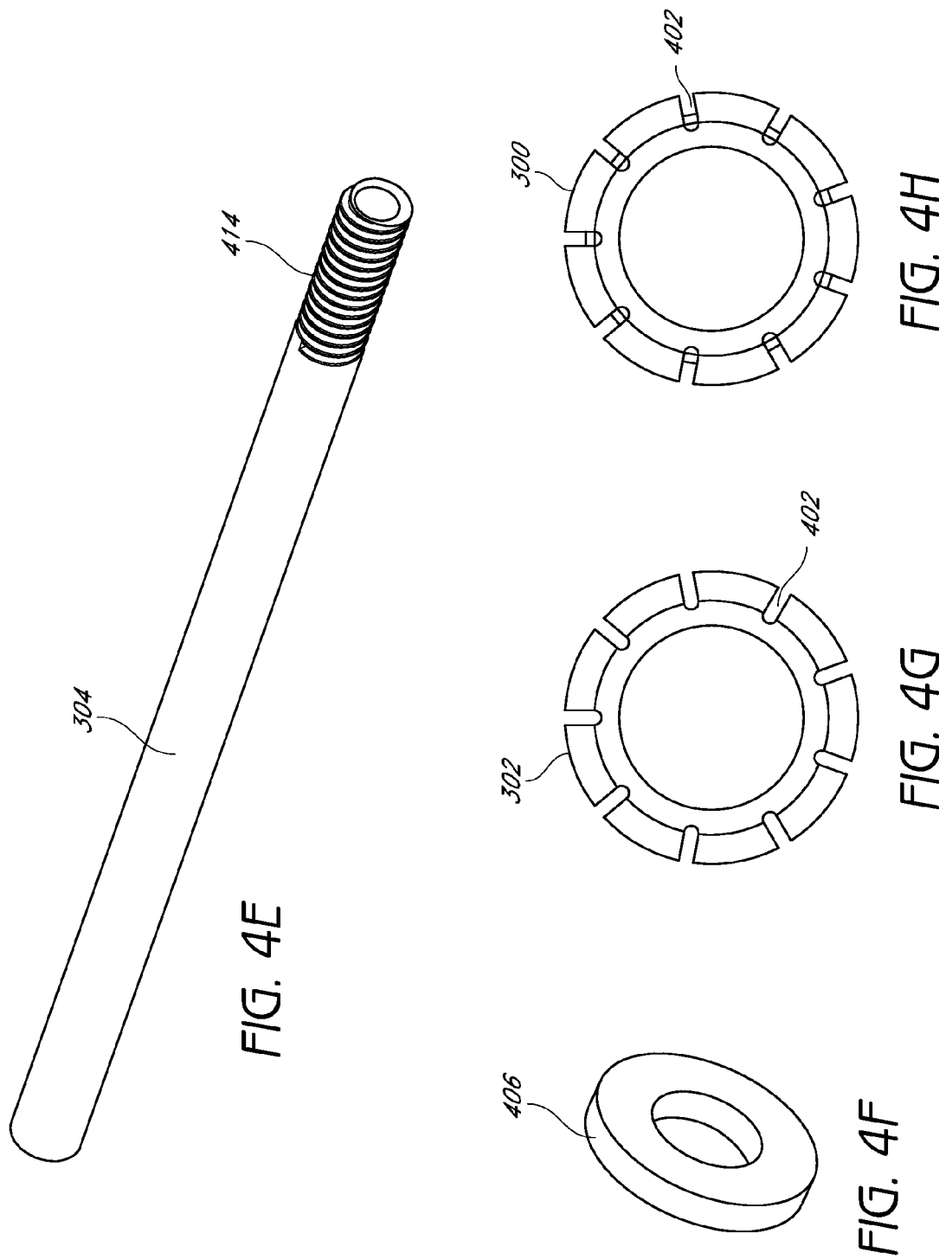

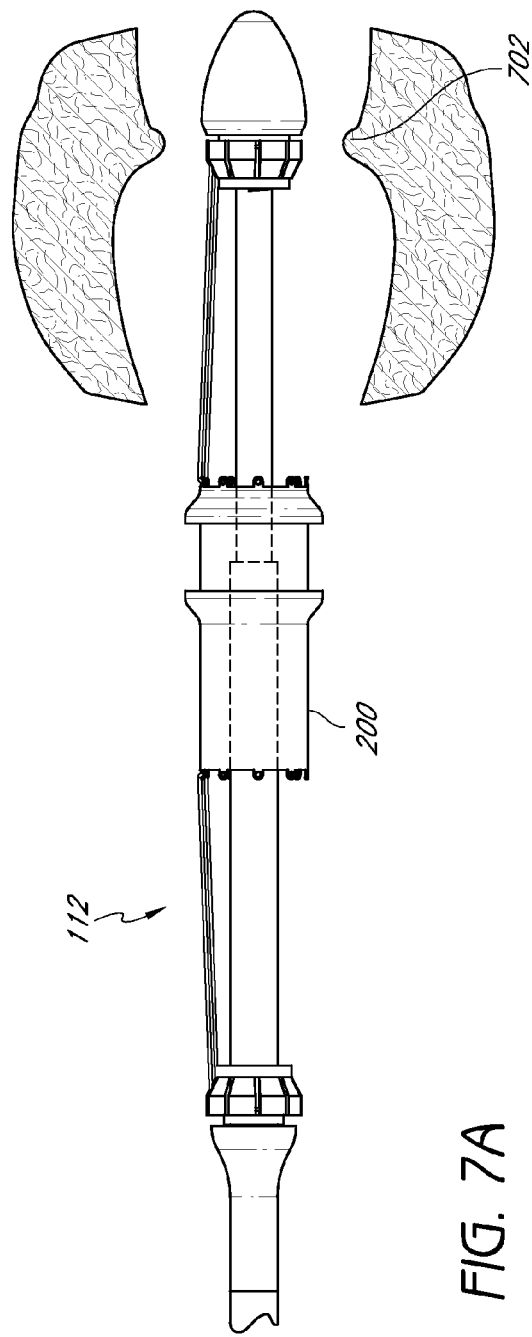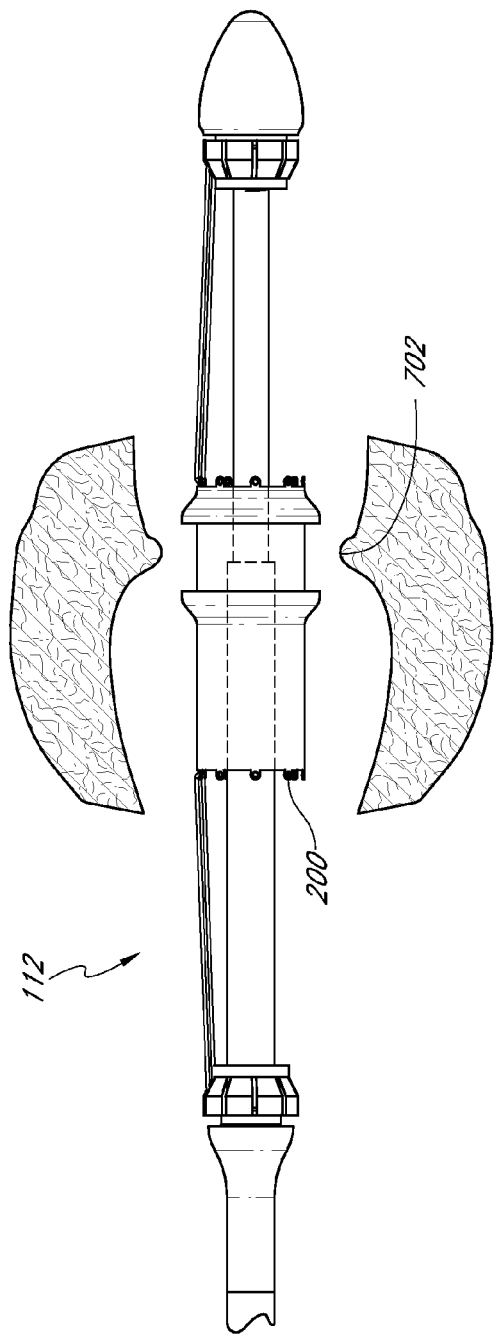
FIG. 7A
FIG. 7B

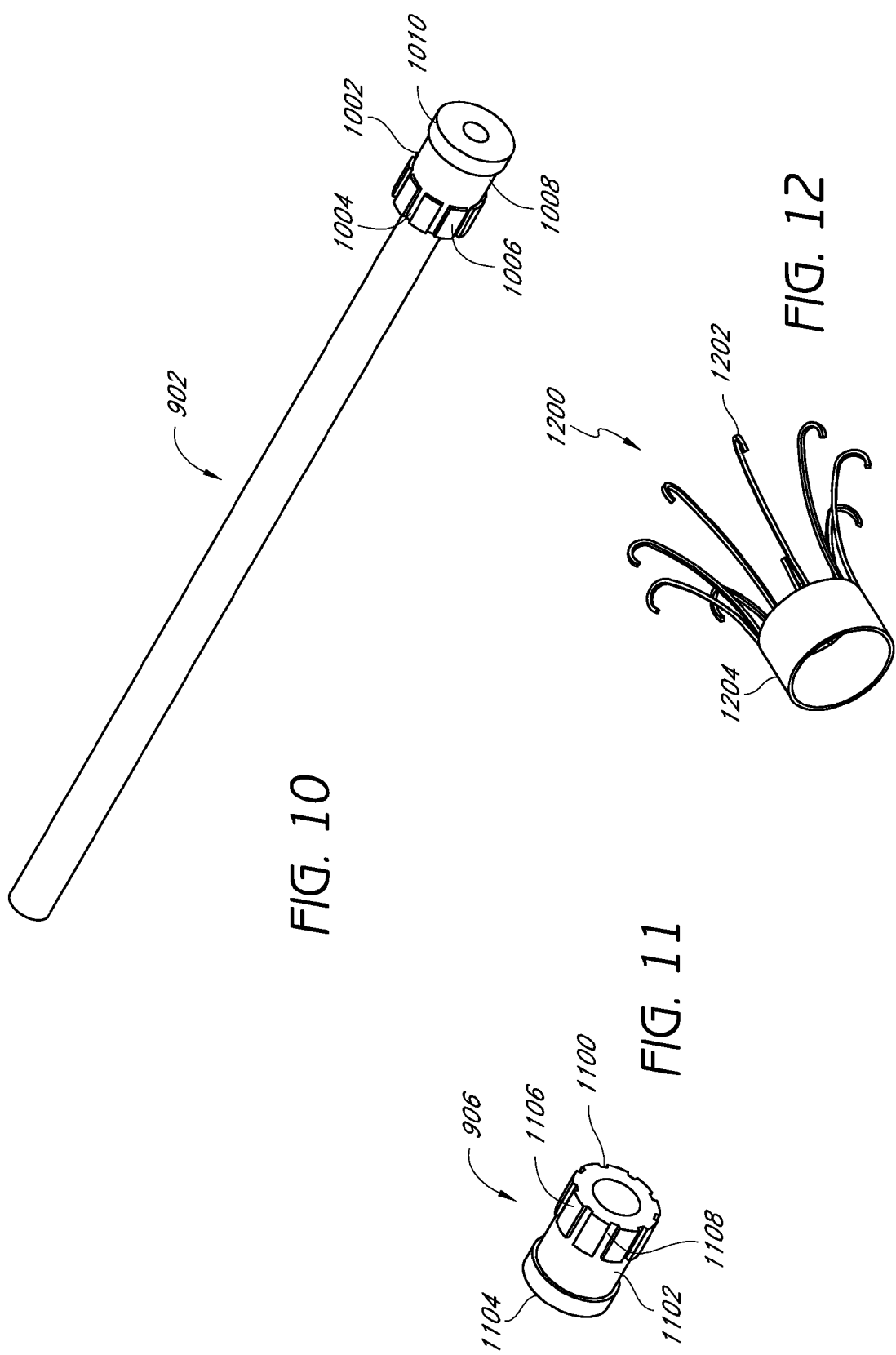

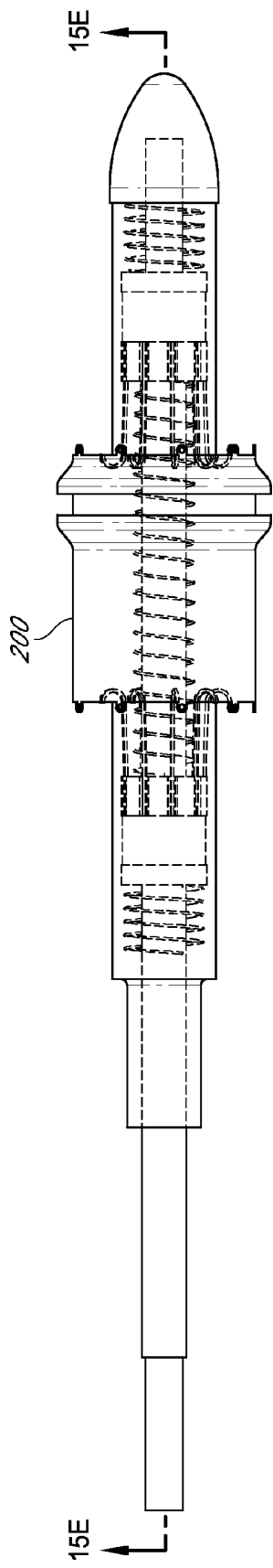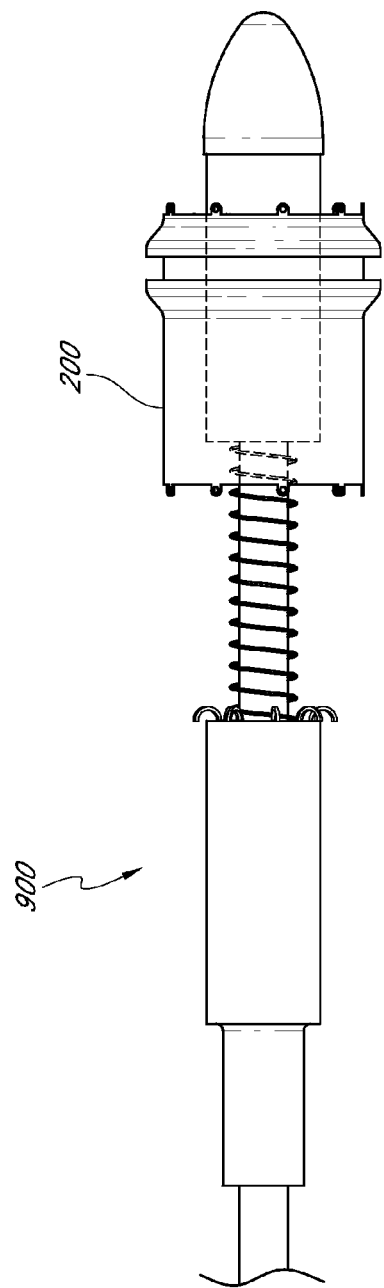
FIG. 15C
FIG. 15D

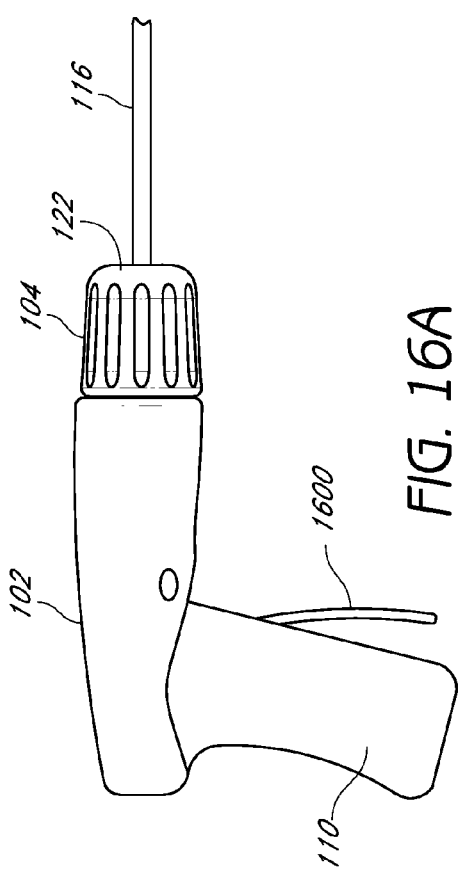
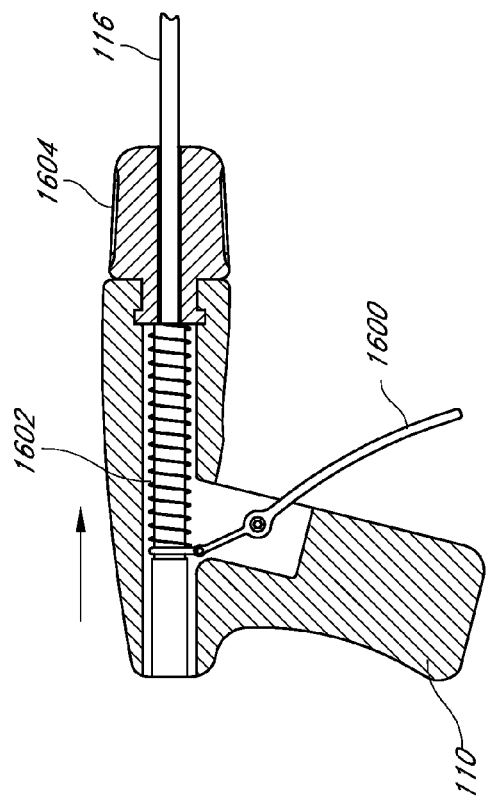

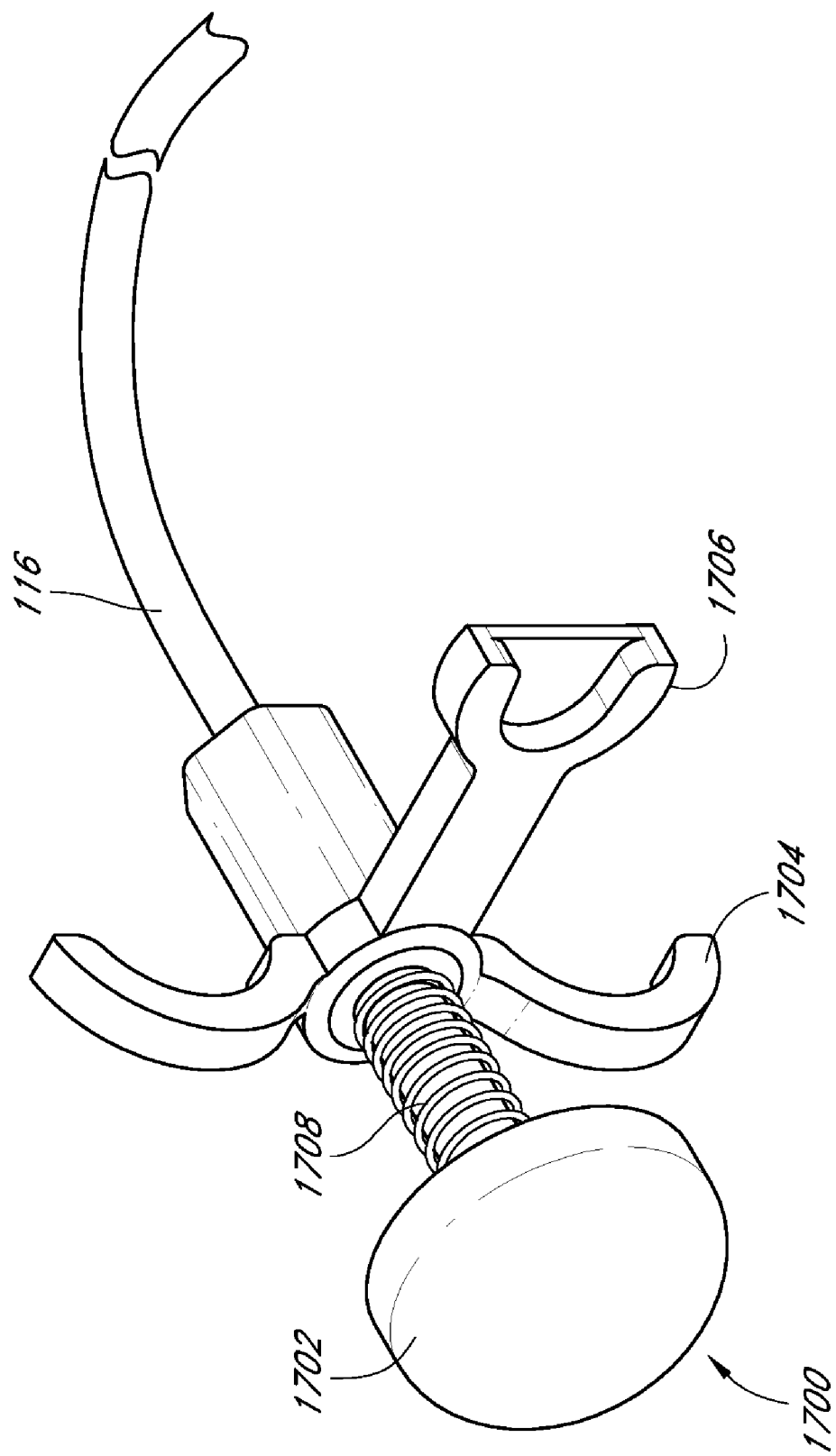

DELIVERY SYSTEM FOR VASCULAR IMPLANT

CROSS-REFERENCE TO RELATED APPLICATIONS

This application claims the benefit of U.S. Provisional Application No. 61/136,760, which was filed on Oct. 1, 2008. The entirety of the priority application is hereby incorporated by reference.

BACKGROUND

1. Field of the Invention

The present invention relates to medical implant insertion delivery systems and, more particularly, to a delivery device for vascular prostheses.

2. Description of the Related Art

Medical implants, in particular stent-based implants, can be deployed in the vasculature of patients to treat a variety of ailments and medical conditions. The fragility of the vascular system tissue and the particular locations where a vascular prosthesis is required necessitates care and precision in the deployment of such implants. In particular, heart related implants, often comprising a valve body supported by a stent frame, present challenges in locating, positioning, and more specifically repositioning of the stent after partial or full deployment of the stent-based implant at a desired location.

A variety of methods and delivery devices aimed at delivering replacement heart valves through percutaneous and minimally invasive approaches currently exist. A primary challenge of known devices, such as those disclosed in U.S. Pat. No. 5,411,552 and U.S. Pat. No. 6,830,584, is the inability to reposition the replacement valve after it is fully deployed. For example, once a stent, or heart valve frame in particular, has been expanded via a balloon catheter, there is no way to reduce the diameter of the heart valve frame again. In another example, to deploy an implant comprising a self-expanding nitinol stent and heart valve body, a delivery device utilizes an outer sheath that is retracted to allow the implant to expand freely to a pre-determined diameter. However, again, once the frame is fully expanded, it cannot be collapsed to adjust, reposition, or remove the implant.

An additional short-coming with the noted delivery systems is that they are designed solely for use with their respective specific valve implant. A further short-coming of such approaches is their reliance on radial force as the primary means of fixation and the inability to accurately position the implant during initial deployment. The aforementioned devices consist of cylindrical frames, lacking features that can locate the implant relative to a native annulus of a heart valve. As a result, these devices must rely on external imaging during the delivery process, which can lead to improper placement of the implant and resulting complications and risks to the patient.

SUMMARY

Accordingly, there is a need in the art for an improved medical implant delivery device that solves some of the disadvantages discussed above. Particularly, there is a need for a delivery device that accurately positions an associated implant in a desired position such as, for example, a native valve annulus, controls the rate at which a frame expands, and allows the implant to be repositioned and adjusted after it has reached its full final diameter upon deployment, and before final release of the implant. Further, a need exists for an improved medical implant delivery device that does not require radial or longitudinal force applied and/or transferred to the abutting contact region of the vascular tissue within the patient.

In accordance with one embodiment, the present invention provides a medical treatment system having an implant that can be positioned and deployed, then undeployed to allow repositioning of the implant while not requiring radial or longitudinal force to be applied to the desired contract region of the vascular system.

In accordance with another embodiment, the present invention provides a medical treatment system comprising a first elongate support member having a distal mount, a second elongate support member having a proximal mount, the second elongate support member being selectively movable relative to the first elongate support member along a longitudinal axis, a self-expanding medical implant that foreshortens upon radially expanding from a radially compacted state, a distal interface configured to attach the distal mount to the implant, and a proximal interface configured to attach the proximal mount to the implant. Moving the distal mount away from the proximal mount applies a longitudinal tension to the implant, causing the implant to expand longitudinally and contract radially and wherein moving the distal mount toward the proximal mount reduces a longitudinal tension in the implant allowing the implant to expand radially toward a fully expanded state.

In another embodiment, the distal mount is attached to the distal interface by at least one distal flexible member and the proximal mount is attached to the proximal interface by at least one proximal flexible member. In one such embodiment, the distal flexible member and the proximal flexible member comprise a suture.

In another embodiment, the distal interface comprises at least one distal eyelet and the proximal interface comprises at least one proximal eyelet.

In yet another embodiment, the medical treatment system additionally comprises a release mechanism configured to release the distal and proximal mounts from the implant.

In yet another embodiment, the distal interface has a length and the implant has a length in the expanded state, and the distal interface length is at least the same as the implant length.

In a further embodiment, the medical treatment system additionally comprises an endoscope that extends through the first elongate support member so as to provide a view adjacent the distal end of the first elongate support member.

In yet another embodiment, a controller controls the movement of the first elongate support member longitudinally relative the second elongate support member.

In another embodiment, an actuator selectively moves the first elongate support member in a longitudinal direction relative to the second elongate support member.

In a further embodiment, the medical treatment system is in combination with a secondary restraint system. In one such embodiment, the secondary restraint system comprises a sheath configured to hold the implant at least partially therein in a compacted state.

In accordance with another embodiment, the present invention provides a medical treatment system that comprises a first elongate support member having a first engagement member and a second elongate support member having a second engagement member, the second elongate support member being selectively movable relative to the first elongate support member along a longitudinal axis. The embodiment further includes a distal mount, a proximal mount slidingly coupled relative to the distal mount along the longitudinal axis, and a first spring interposed between the proximal and distal mounts so as to bias the proximal and distal mounts longitudinally away from one another. The embodiment additionally includes a self-expanding medical implant that foreshortens upon radially expanding from a radially compacted state, a distal interface configured to attach the distal mount to the implant, and a proximal interface configured to attach the proximal mount to the implant. Moving the distal mount away from the proximal mount applies a longitudinal tension to the implant causing the implant to expand longitudinally and contract radially and wherein moving the distal mount toward the proximal mount reduces a longitudinal tension in the implant allowing the implant to expand radially toward a fully expanded state.

In another embodiment, the proximal and distal mounts are arranged between the first and second engagement members.

In yet another embodiment, at least one of the proximal and distal interfaces comprises a ring assembly having at least one flexible arm fixedly attached to the ring at a first end and releasably attached to the implant at a second end, the second end extending beyond the diameter of the ring, and wherein the at least one flexible arm is resilient.

In a further embodiment, the first and second engagement members are configured so that as the first and second engagement are moved toward one another, the proximal and distal mounts are urged toward each other and the biasing of the center spring is overcome so that the implant contracts longitudinally and expands radially.

In one such embodiment, a second spring is interposed between the second engagement member and one of the proximal and distal mounts, and a third spring is interposed between the first engagement member and the other of the proximal and distal mounts, and the second and third springs each have a spring constant greater than a spring constant of the first spring.

In another such embodiment, the spring constants of the second and third springs are substantially the same.

In accordance with another embodiment, the present invention provides a method of delivering a medical implant. The method includes providing an implant delivery system comprising a self expanding implant configured to longitudinally foreshorten upon radially expanding from a compacted radial state, a delivery device comprising proximal and distal mounts that selectively connect to the implant by a proximal and a distal interface, respectively, the delivery device configured so that the proximal and distal mounts can be selectively moved relative to one another so as to selectively apply a longitudinal tension on the implant to urge the implant into the compacted radial state. The embodiment further includes advancing the implant in a compacted radial state within a patient to a desired deployment location, positioning the implant adjacent the desired deployment location, actuating the delivery device so as to move the proximal and distal mounts toward one another so as to reduce the longitudinal tension on the implant and allow the implant to radially expand toward a fully expanded state, and verifying the implant is properly positioned at the desired deployment location within the patient.

Another embodiment, wherein if it is determined that the implant is not properly positioned, additionally comprises moving the proximal and distal mounts away from one another so as to increase the longitudinal tension on the implant to longitudinally expand and radially contract the implant so as to disengage the implant from the patient's tissues. A further such embodiment additionally comprises adjusting the position of the implant, and again moving the proximal and distal mounts toward one another so as to allow the implant to radially expand.

Yet another embodiment additionally comprises verifying whether the implant is poised to be properly positioned after partially expanding the implant.

A further embodiment additionally comprises providing an endoscope, and using the endoscope to verify whether the implant is properly positioned.

Other inventive embodiments and features are disclosed below.

BRIEF DESCRIPTION OF THE DRAWINGS

FIG. 3A is a side view of a distal assembly of the medical treatment system of FIG. 1.

FIG. 3B is a cross-section view of the distal assembly of the medical treatment system of FIG. 3A.

FIGS. 4B-4H show additional views of detail elements of the delivery device shown in FIG. 4A.

FIGS. 7A-C are side views of the insertion and deployment of an implant of the medical treatment system of FIG. 1 at certain stages of operation.

FIG. 10 is a perspective view of an elongate support member of the medical treatment system of FIG. 9.

FIG. 11 is a perspective view of a mount ring of the medical treatment system of FIG. 9.

FIG. 12 is a perspective view of a flexible member assembly of the medical treatment system of FIG. 9.

FIGS. 15A-D are side views of the medical treatment system of FIG. 9 shown at certain stages of the insertion and deployment of an implant.

FIGS. 16A-B are side views of alternative controllers of the medical treatment system in accordance with the present invention.

FIG. 17 is a side view of an alternative controller of the medical treatment system in accordance with the present invention.

DETAILED DESCRIPTION OF PREFERRED EMBODIMENTS

The associated drawings and specification discuss aspects and features of the present invention in the context of several different embodiments of implant delivery devices and methods that are configured for use in the vasculature of a patient. Discussing these features in connection with heart valve implants employing stents provides for clarity and consistency in presenting these inventive features and concepts. However, it is to be understood that the features and concepts discussed herein can be applied to products other than stented heart valve implant. For example, the controlled positioning, deployment, retraction, and repositioning features described herein can be applied to medical implants for use elsewhere in the body, such as within the coronary arteries, the digestive tract, or the like.

In fact, the principles discussed herein can be used in any application that would benefit from a prosthesis delivery device having repositioning capability and/or a reduced or negligible radial load transferred to the adjacent tissue surface during deployment of the prosthesis. While Applicant specifically provides examples of use of these principles in accordance with medical implant delivery devices and specifically delivery of stents, Applicant contemplates that other applications may benefit from this technology.

Figure 1:
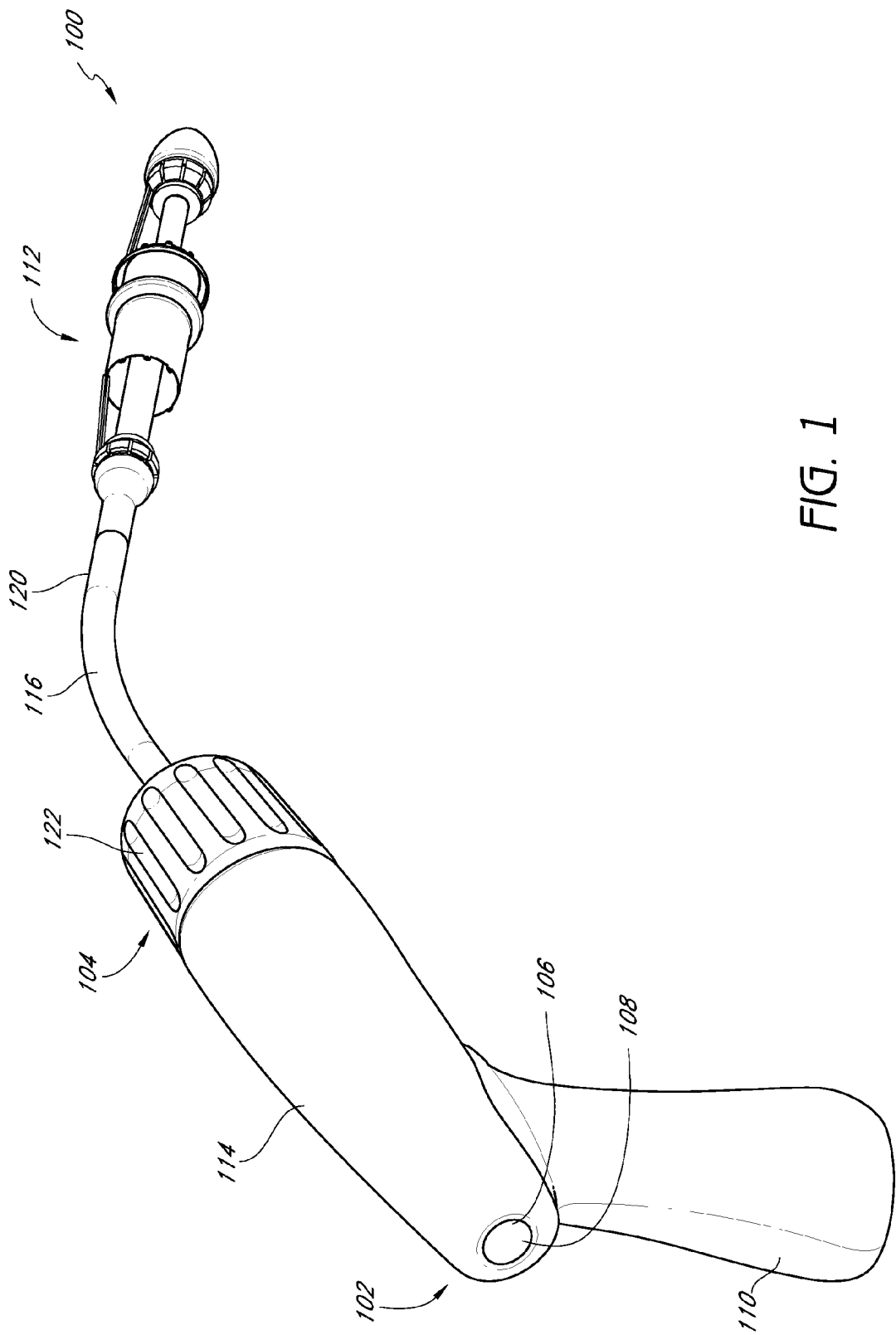
FIG. 1 is a perspective view of a medical treatment system in accordance with an embodiment of the present invention.

With reference to FIG. 1, a perspective view of a medical treatment system 100 is shown. The medical treatment system 100 generally includes a controller 102, otherwise referred to as a handle, and a distal assembly 112. The handle 102 includes a barrel 114 with a grip 110 located adjacent a proximal end of the barrel 114. The handle 102 further includes an actuator 104 located adjacent a distal end of the barrel. The barrel 114 is affixed to a top most portion of the grip 110. An access to a lumen 106 is provided at the proximal end of the barrel 114. The grip and barrel are sized to fit a typical physician's, or user's, hand to provide a stable grip and operating characteristics. Further, the shape and size of the barrel and grip are ergonomically shaped to provide a safe and reliable hold for the user. These features of the handle 102 are utilized to control the insertion and deployment of the distal assembly 112 and successfully implement the medical treatment system 100.

The lumen 106 extends through the barrel 114 from the proximal end to the distal end, terminating at the actuator 104, and providing the outlet and coupling interface for a flexible portion 116, otherwise referred to as a proximal catheter. The proximal catheter is coupled to the handle 102 at a proximal end and is coupled to the distal assembly 112 at a distal end, establishing mechanical communication between the handle and the distal assembly. The actuator, as depicted in the illustrated embodiment, includes a rotating knob 122 that, depending on the direction of rotation, will longitudinally move elements of the proximal catheter 116 relative the handle. The elements of the proximal catheter 116 can be moved toward and into, or away and out of, the handle 102. Alternatively, the proximal catheter can be substantially rigid, providing added control to the positioning of the distal assembly during the insertion and deployment operations discussed further below.

The distal assembly 112 is coupled to the handle 102 via the proximal catheter 116, the length of which can vary according to a physician's needs. The proximal catheter includes a flexible extension tube 118, as shown in FIG. 3A, and a flexible sheath 120. The flexible sheath includes a through-hole, or lumen, disposed about a longitudinal axis along the full length of the sheath. The flexible sheath provides a protective cover layer over the surface of the flexible extension tube 118, yet allows the flexible extension tube 118 to slidingly move longitudinally within the sheath. The flexible extension tube is a catheter having a lumen disposed about a longitudinal axis. The flexible extension tube proximal end is engagingly coupled to the actuator 104 and handle 102. The flexible sheath proximal end is fixedly attached to the distal end of the barrel 114 adjacent the actuator 104. The distal end of the flexible sheath is fixedly attached to the distal assembly 112. Thus, the length of the flexible sheath establishes the distance between the handle 102 and the distal assembly. In alternative embodiments the flexible extension tube and/or the flexible sheath can be substantially rigid.

With continued reference to FIG. 1, the illustrated embodiment of medical treatment system 100 is generally intended for minimally invasive procedures, thus the free length of the proximal catheter 116 between the distal assembly 112 and the handle 102 is shorter than if the system were primarily directed to a percutaneous procedure to access a desired location for deployment of the medical implant. However, the free length of the proximal catheter 116 can be longer, as the medical treatment system can be utilized in percutaneous procedures in alternative embodiments of the system.

The lumen 106, in addition to providing an extended path of motion for the proximal catheter 116 flexible extension tube 118, also provides a path and guideway for an endoscope 108. The endoscope is used to provide a physician visual access adjacent to the distal assembly 112 during the deployment operation of the medical treatment system 100 and is directed through the lumen 106 and the flexible extension tube to the distal assembly.

Figure 2B:
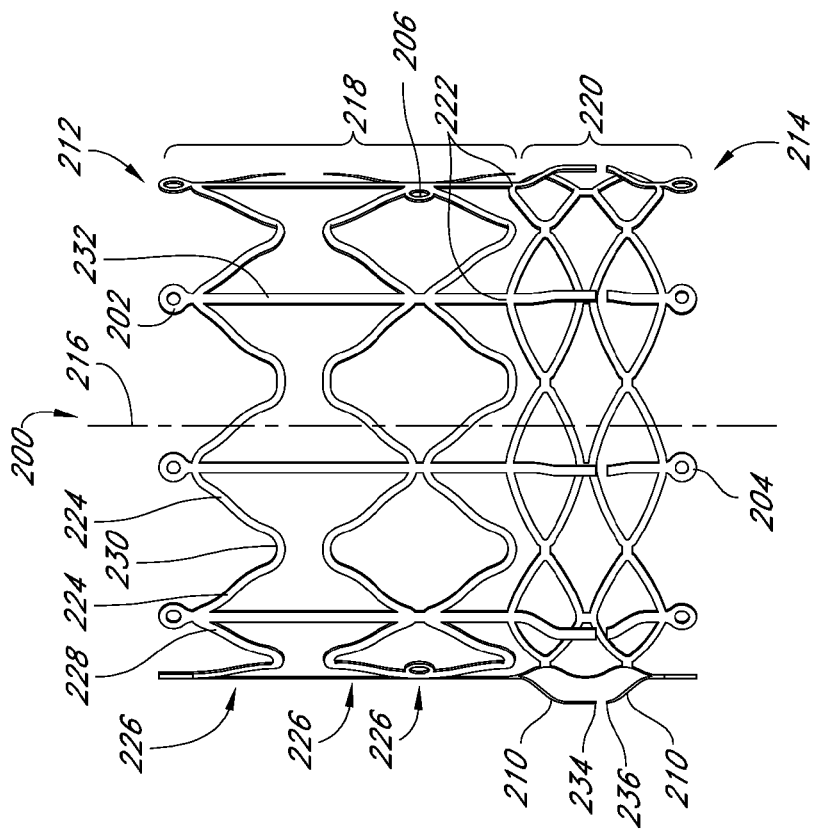
FIG. 2B shows the stent frame of FIG. 2A in an expanded state.
Figure 2A:
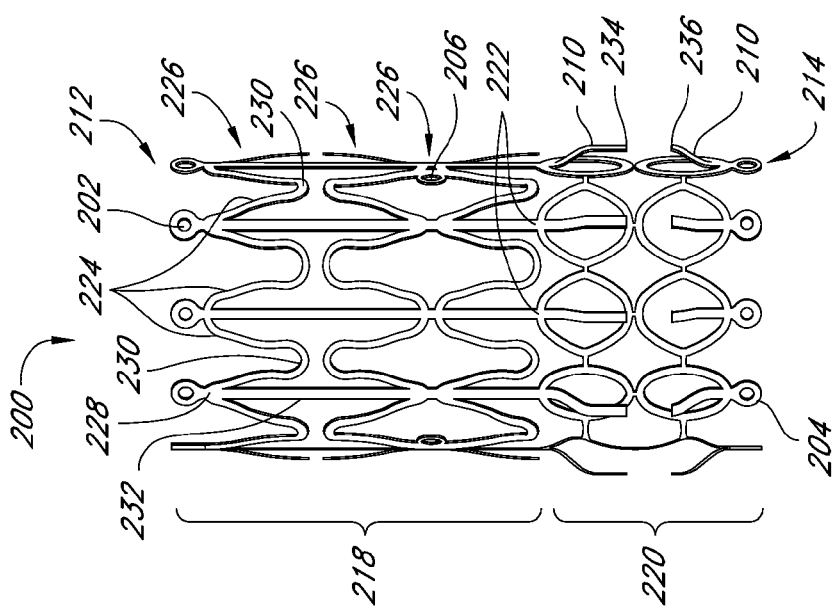
FIG. 2A is a side view of a stent frame shown in a compacted state.

With reference to FIGS. 2A and 2B, a front view of a medical implant 200, otherwise referred to as a stent, is shown. In the illustrated embodiment, the implant 200 is configured to allow foreshortening of the frame body upon the longitudinal contraction of the implant 200. The implant 200 includes a frame 208, legs 210, otherwise referred to as anchors, a proximal interface 202, a distal interface 204, and an intermediate interface 206. FIGS. 2A and 2B only show a frontside view of the implant 200 details, omitting the backside structure of the see-through device for clarity. Additionally, reference to implant 200 in further figures is depicted as a simpler cylinder shaped device for clarity and simplicity purposes only.

In a preferred embodiment, the illustrated implant 200 supports a heart valve body, and can be expanded from a compacted state as shown in FIG. 2A to an expanded state as shown in FIG. 2B. The illustrated implant 200 preferably is a self-expanding stent constructed of a flexible material, preferably a shape memory material such as nitinol. As the implant is self-expanding, the implant 200 is in a fully opened state, as depicted in FIG. 2B, when relaxed in an unrestrained condition. The illustrated implant 200 preferably is elongate from a proximal end 212 to a distal end 214 and is tubular with a longitudinal axis 216 and a generally circular cross section. It is to be understood that in other embodiments stents can have a non-circular cross section, such as a D-shape, an oval or an otherwise ovoid cross-sectional shape. In the illustrated embodiment a plurality of spaced apart proximal interfaces 202 are provided at the proximal end 212 and distal interfaces 204 are provided at the distal end 214 of the implant 200. Other embodiments may be constructed without proximal or distal interfaces 202, 204.

The illustrated implant 200 has a non-foreshortening portion 218 and a foreshortening portion 220. The portions are joined at a transition 222 between the proximal and distal ends 212, 214. Foreshortening refers to a behavior in which the length of the implant 200 in the foreshortening portion 220 decreases as the radius of the stent increases from the compacted state to the expanded, deployed state. As such, in FIG. 2A, which shows the implant 200 in a compacted state, the foreshortening portion 220 of the implant 200 is longer than when the stent is in the expanded state illustrated in FIG. 2B.

The illustrated implant 200 has a plurality of anchors 210 that extend from the transition 222 into the foreshortening portion 220. Additional anchors 210 also extend from adjacent the distal end 214 into the foreshortening portion. The anchors extending in opposite directions establish a gap between their respective free ends, or proximal tip 234 and distal tip 236. The longitudinal contraction of the implant creates a corresponding movement of the anchor 210 that moves the proximal and distal tips closer together. The movement together allows the anchors 210 to grasp onto tissues at a desired location so as to hold the implant in place.

With continued reference to FIG. 2B, the non-foreshortening portion 218 of the illustrated implant 200 comprises a plurality of rows or rings 226a-c of circumferentially expansible elements, or struts 224, arranged in a zigzag pattern. The struts 224 are configured to expand and contract with a change in radius of the implant 200. In the illustrated embodiment, the stent has three such rings 226a-c. It is to be understood that more or fewer rings can be employed as desired to accomplish the purposes of this stent frame. In the illustrated embodiment, the respective ends of each circumferential undulating strut 224 joins an adjacent strut 224 at an apex 228, 230 which is, in at least some embodiments, an area of preferential bending. In the illustrated embodiment, the zigzag pattern of a first 226a and a third ring 226c are generally in phase with one another, while the struts 224 of a second ring 226b between the first and third rings 226a, 226b are generally out of phase with those of the first and third rings. It is to be understood that, in other embodiments, all or most of the rings can be in phase with one another or out of phase as desired.

With continued reference to FIG. 2B, longitudinal struts 232 extend transversely across the rings 226a-c of the non-foreshortening portion 218 from the proximal end 212 of the implant 200 to the transition 222. More particularly, each ring 226 shares a common longitudinal strut 232. The longitudinal struts 232 extend through apices 228 of adjacent rings 226, and preferably extend the entire length of the nonforeshortening portion 218. Preferably, the longitudinal struts 232 comprise a nonexpandable rod or bar. The apices 228 that are connected to the longitudinal struts 232 are referred to as "connected" apices 228. Apices 230 not connected to longitudinal struts 232 are referred to as "free" apices 230.

As noted above, the longitudinal struts 232 are not substantially expandable in a longitudinal direction. As such, even though the undulating struts 224 provide flexibility in radial expansion or compaction, as the implant 200 changes radial size between the compacted and expanded states, the longitudinal length of the stent in the nonforeshortening portion 218 remains substantially unchanged.

With reference to FIGS. 3-6, several views of an embodiment of the distal assembly 112 and its details are shown. The distal assembly includes the implant 200 and a delivery device 316. The delivery device 316 further includes a proximal mount 300, a distal mount 302, a first elongate support member 304, a second elongate support member 306, a flanged sleeve 404, a distal collar 406, and a distal body 308. The delivery device 316 is used to accurately and safely deliver and deploy the implant, or stent, adjacent a desired location within the patient.

The first elongate support member 304, otherwise referred to as a pull rod or distal catheter, is an elongate member preferably having a degree of flexibility but maintaining adequate stiffness to be axially loaded in compression and tension. The pull rod 304 includes a lumen extending along its full length, similar to a common catheter. The pull rod 304 is typically made of a flexibly capable bio-compatible material for use in the human body, e.g. silicone, polyurethane, polyethylene, polychloroethene, polytetrafluoroethylene, or the like. The pull rod 304 is generally longer and extends distally beyond the distal end of the second elongate support member 306. In the illustrated embodiment of FIG. 4E, the distal end of the pull rod 304 includes an external thread 414 for coupling to an atraumatic nose cone or distal body 308, as discussed in detail below. The proximal end of the pull rod is coupled to the proximal catheter 116 distal end via the flexible extension 118, also discussed in further detail below.

Figure 4A:
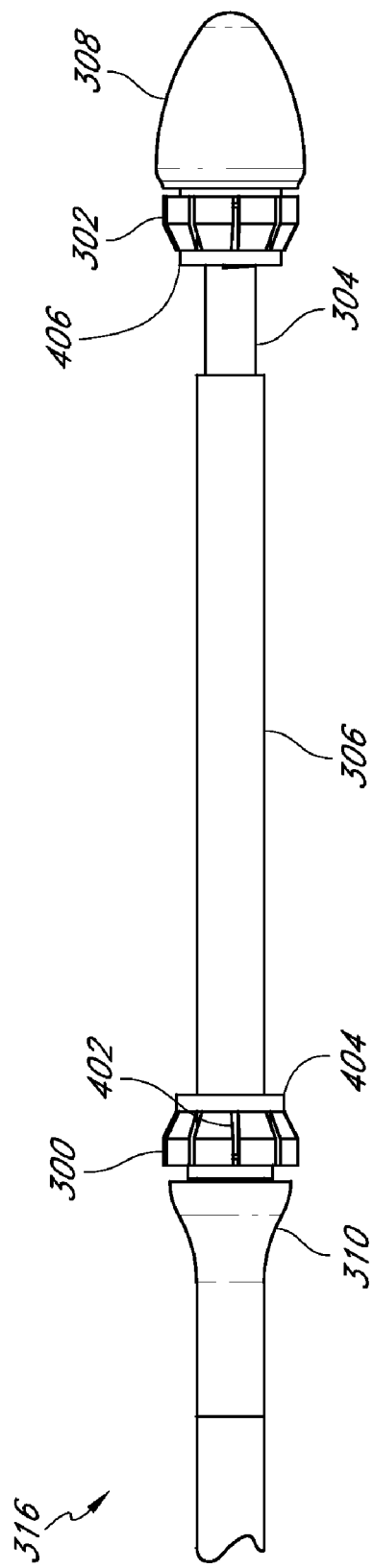
FIG. 4A is a side view of a portion of a delivery device of the medical treatment system of FIG. 1.
Figure 4C:
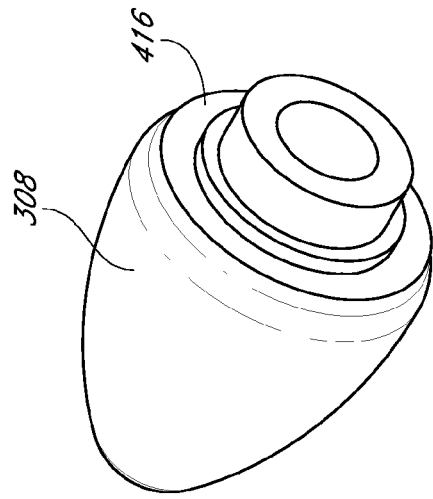

With continued reference to FIGS. 3-6, the second elongate support member 306, otherwise referred to as a proximal stop, is a rigid cylinder having an inner diameter with a diametral magnitude at least the same as the pull rod 304, and a support 310 that is integral to the cylinder, as illustrated in FIG. 4A. The proximal stop 306 is typically made of a rigid bio-compatible material for use in the human body, e.g. titanium, stainless steel, thermoplastic or thermoset resins, ceramic, or the like. The proximal stop 306 is shorter than the pull rod 306, generally being one to two times longer than the implant 200 although other varying lengths are possible. The pull rod 304 is slidingly engaged within the inner diameter of the proximal stop 306, as described in detail below, and extends distally out of the distal end of the proximal stop 306 at least ½ to 2 times the longitudinal length of the implant when the distal assembly is in a longitudinally extended arrangement, or configuration.

Figure 6:
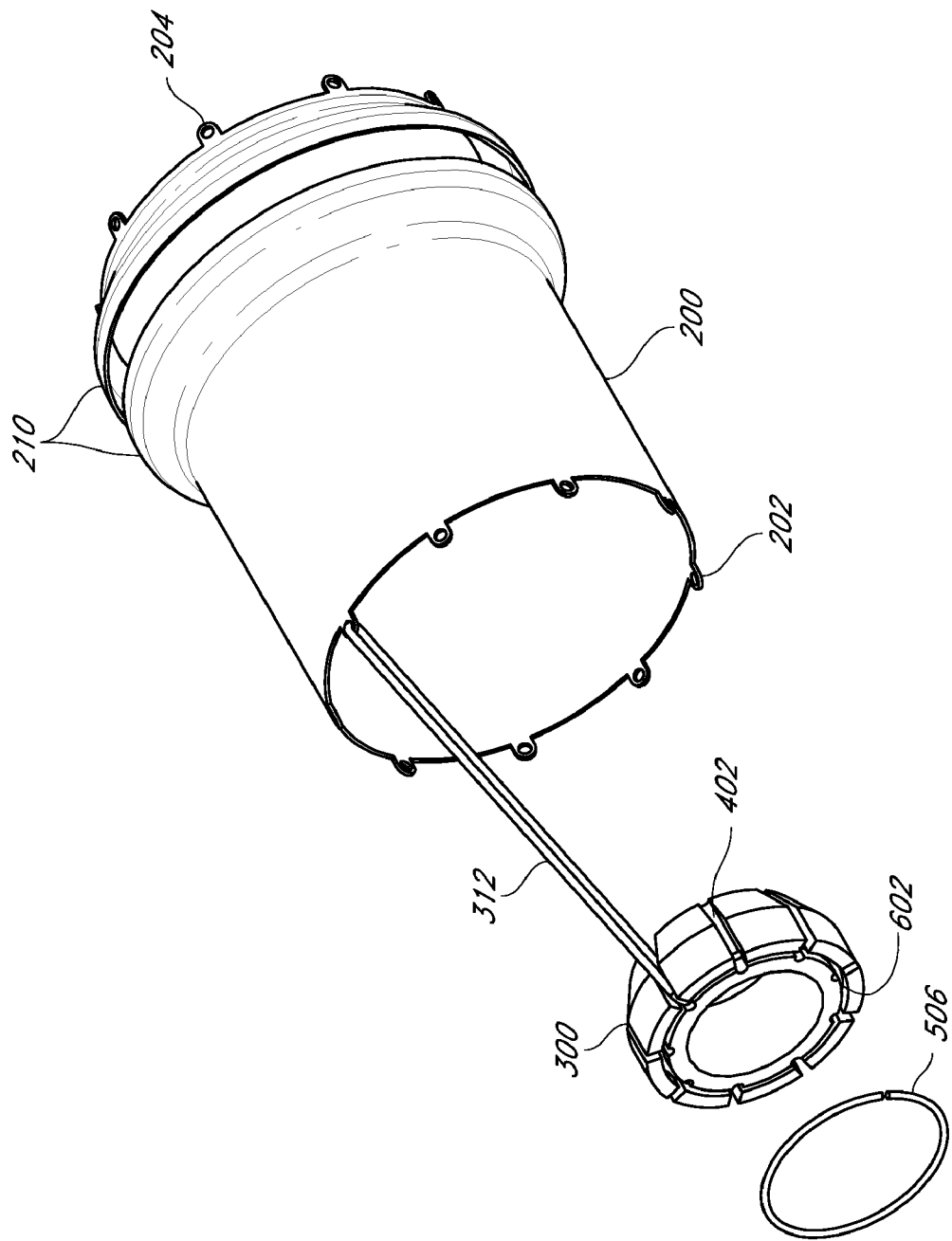
FIG. 6 is an expanded view of a portion of the medical treatment system of FIG. 1.

With particular reference to FIG. 6, the proximal mount 300 is a ring shaped device having an interior through-hole disposed about a longitudinal axis, an inner surface, an outer surface, a proximal face, a distal face, at least one guideslot 402, and an annular groove 602. The through-hole establishes the diameter of the inner surface, and the inner surface diameter is substantially the same or slightly greater than the outer cylinder surface of a flanged sleeve 404, as depicted in the illustrated embodiment of FIG. 4. The radial thickness of the proximal mount 300 preferably tapers from a thicker portion at the proximal face to a thinner portion at the distal face. Thus, the proximal face of the proximal mount has a greater surface area, corresponding to the larger wall thickness of the ring member proximal end, as compared to the distal face of the proximal mount 300.

An annular groove 602, depicted in the illustrated embodiment of FIG. 6, is located on the proximal face of the proximal mount 304. The annular groove 602 extends all around the proximal face, encircling the through-hole about the longitudinal axis, and having a depth sufficient enough to receive a proximal ring 506. The guideslot 402 is more clearly depicted in the illustrated embodiment of FIGS. 4 and 6. The at least one, or alternatively a plurality of, longitudinal grooves, or guideslots 402, are located on the outer surface of the proximal mount 304. The guideslot preferably has a depth that is less than the total thickness of the proximal mount, and thus does not extend depthwise through to the inner surface of the proximal mount 300. The plurality of guideslots 402 will generally be equally spaced circumferentially about the proximal mount, although any spacing arrangement is possible.

The proximal mount 300 and the distal mount 302 have similar or identical characteristics that are symmetric about the implant 200, thus in the illustrated embodiment the description of the proximal mount applies accordingly to the description characteristics of the distal mount except as expressly described. In particular, the through-holes of the distal mount 302 and the proximal mount 304 can be different in diametral size where they are coupled to differing sized mounting elements, such as the diameter of the neck on the distal body 308, with which the distal mount is coupled, or the flanged sleeve 404, with which the proximal mount 300 is coupled, as described in detail below.

Figure 4D:
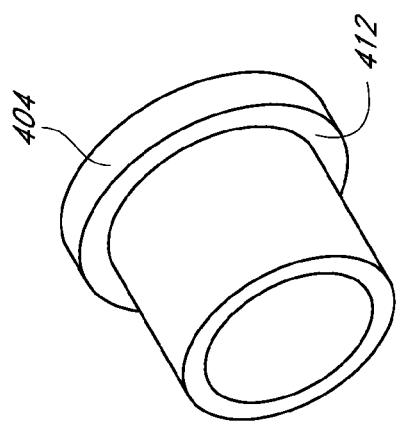

With continued reference to FIGS. 4A, 4D and 4F, an embodiment of the flanged sleeve 404 and the distal collar 406 are shown. The flanged sleeve 404 is a substantially cylindrical member having a flange, or lip, portion protruding radially outward from the outer surface of the cylinder and located adjacent the distal end of the flanged sleeve 404. The inner surface of the flanged sleeve 404 establishes a through-hole disposed about a longitudinal axis. The diameter of the through-hole is substantially the same as, or slightly greater than, the outer surface diameter of the proximal stop 306. The outer surface diameter of the proximal flanged sleeve cylindrical portion is substantially the same, or slightly less than, the inner surface diameter of the proximal mount 300. The cylindrical body of the flanged sleeve 404 extends a longitudinal length that is longer than the longitudinal length of the proximal mount 300.

In the illustrated embodiment, the distal collar 406 is a ring, similar to a washer or a nut, having a through-hole disposed about a longitudinal axis. The longitudinal thickness of the collar 406 is sufficient to include internal fastener threads on the inner surface diameter of the through-hole. The hole is sized substantially the same as pull rod 304. The collar 406 is made from a rigid, bio-compatible material, e.g. metal, plastic, Teflon, or the like. Alternatively, the collar can be fabricated from a flexible member that deflects radially outward further than a rigid collar yet sufficiently capable of retaining the distal mount on the nose cone, e.g. a radial spring, an elastic material such as rubber, or the like.

The distal body 308, otherwise referred to as a nose cone, as best shown in FIGS. 3 and 4, is generally a cone or frustum shaped, bullet nosed structure with bulbous rounded surfaces to advantageously provide an atraumatic gentle entry and movement within the patient's vasculature and mitigate the risk of injury to adjacent tissue due to the insertion of the distal assembly 112 within the patient. The cone shaped structure of the nose cone 308 is disposed about a longitudinal axis, with the larger diameter base of the cone located adjacent a proximal end of the nose cone 308 and the decreasing, tapering, or arcing, diameter extends to a generously rounded distal end, or tip, of the nose cone 308.

Figure 4B:
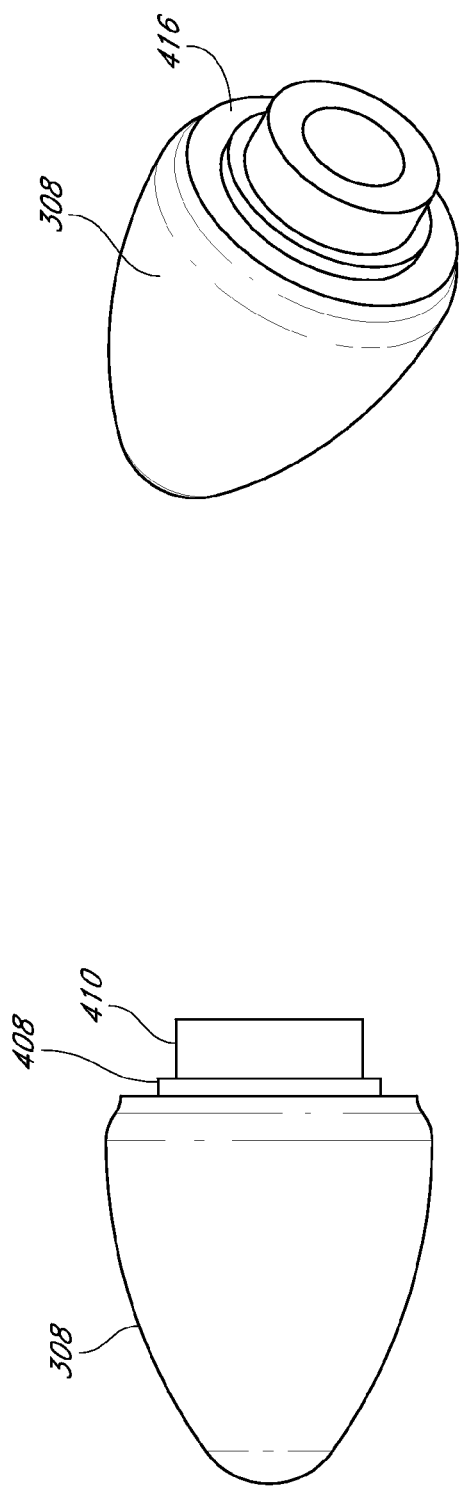

With continued reference to FIGS. 4A-B, the nose cone 308 includes a through-hole disposed about the longitudinal axis along the full length from the proximal end to the distal end. The through-hole diameter is similar in magnitude to the inner diameter of the pull rod 304. The nose cone 308 proximal end, or proximal face 416, also includes a flange 408 and a neck 410 that extend proximally from the proximal end of the cone 308, and are substantially centrally disposed about the longitudinal axis of the nose cone 308. The flange has a diameter smaller than the cone but larger than the neck. The flange extends proximally a sufficient amount to create a shallow lip, such that a small gap exists when the distal mount is installed on the neck 410, as described in detail below. The neck extends even further proximally, establishing a proximally protruding cylinder off of the nose cone 308. The neck has a smaller outer diameter than the flange and also includes internal fastener threads adjacent the proximal end.

The through-hole of the nose cone 308 provides an access point for the endoscope 108, allowing the endoscope to pass through and exit out of the distal end, after which the endoscope 108 can then look back proximally on the distal assembly 112 and the implant 200 to provide visualization of the deployment process. An alternative embodiment of the nose cone 308 includes an internal configuration providing an arcuate path, within the cone 308 itself, and exiting for example out of the side of the cone 308. Such a configuration routes the endoscope 108 viewing tip back toward the implant prior to exiting the distal end of the nose cone 308, placing the viewing tip nearer the implant. The endoscope 108 can similarly exit any surface of the cone 308 that is sufficient to provide a visualization of the implant. In further embodiments, an aperture or viewing port can be formed in the pull rod 304 to enable an endoscope 108 to view the implant.

With reference to FIGS. 3 and 4A, the side view of delivery device 316 further shows an embodiment of the support 310. The support 310 is an integral lip extending all around the proximal stop 306 and located adjacent the proximal end of the proximal stop 306. The support 310 has a substantially flat surface on the distal face, the face also being substantially normal to the longitudinal axis of the proximal stop 306. The proximal face of the support 310 has a tapered surface extending from the radially outermost surface, or diameter, of the support 310 to the outer surface of the proximal stop 306 cylindrical surface. As will be discussed below, the support 310 provides a physical stop and support for the proximal mount 300 disposed about the proximal stop 306, preventing the proximal mount from sliding or moving too far proximally as well as locating the proximal mount for installation of implant 200 onto delivery device 316.

With continued reference to FIG. 3, the side view of delivery device 316 further shows the proximal flexible member 312, otherwise referred to as a proximal suture, and the distal flexible member 314, referred to as a distal suture. In the illustrated embodiment, the sutures 312, 314 attach the implant/stent 200 to the delivery device 316. The length of the sutures 312, 314 can vary according to the size and location of the stent 200 and the delivery device 316. The diameter of the sutures 312, 314 can vary as well, provided the sutures 312, 314 can sustain the tensile loads required for the implant installation and deployment process. The sutures 312, 314 preferably are made of typical bio-compatible suture materials, e.g. nylon, polypropylene, polyglycolic acid, polyethylene, other thermoplastic polymers, cotton, silk, or the like. As will be discussed below, a plurality of sutures 312, 314 are used to attach the implant to the delivery device 316, as attachment is made at both the proximal and distal ends of the implant and the implant preferably is substantially centered about the delivery device 316. In alternative embodiments the flexible members can have differing configuration, can be made of other materials, and may be substantially rigid.

Figure 5:
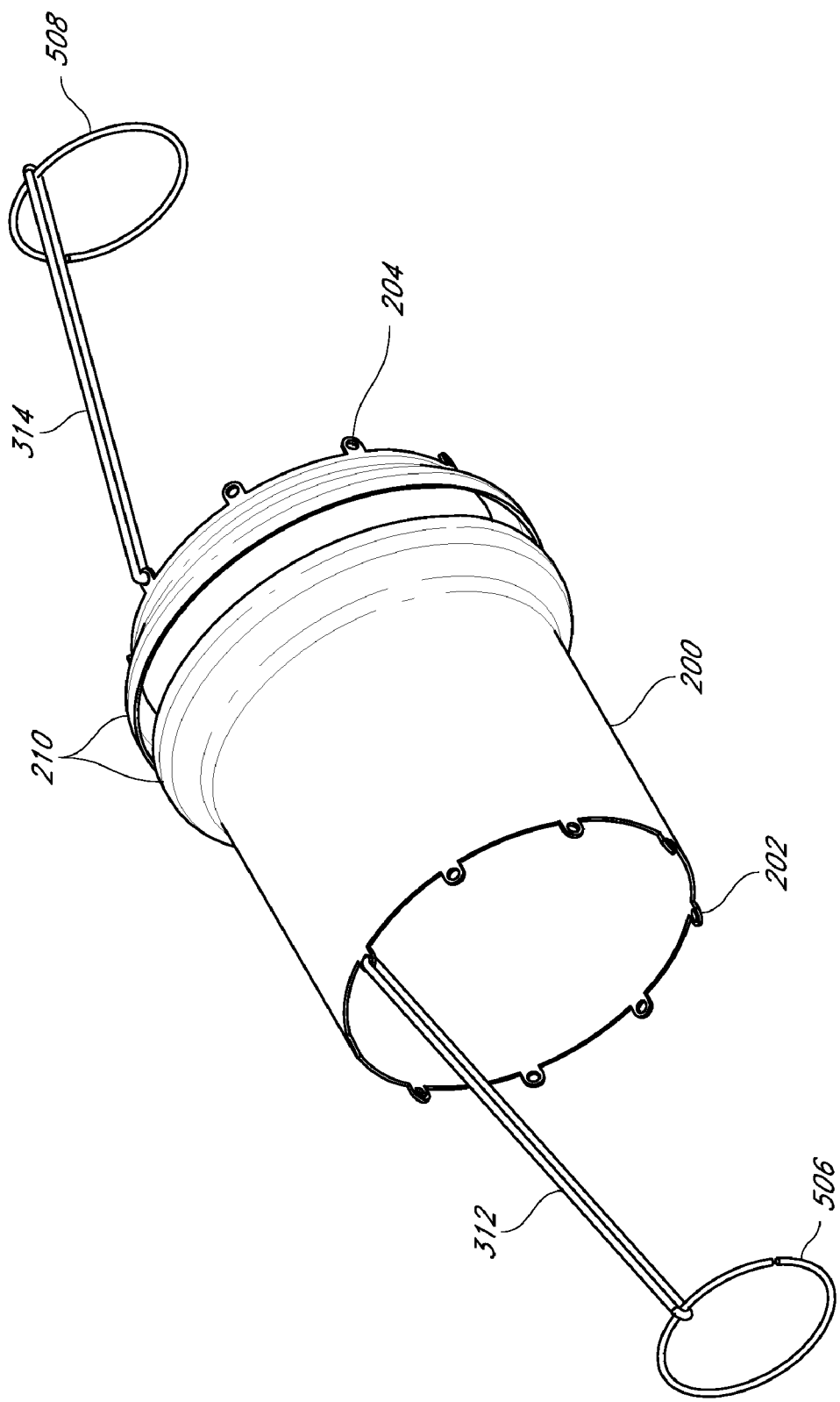
FIG. 5 is a perspective view of a portion of the medical treatment system of FIG. 1.

With reference to FIGS. 5 and 6, a perspective view of selected details of the distal assembly 112 are shown, which includes a proximal ring 506, a distal ring 508, the proximal interface 202, and the distal interface 204, the anchor 210, and an annular groove 602. The proximal ring 506 and the distal ring 508, otherwise referred to as proximal snap ring and distal snap ring, respectively, have similar characteristics in the illustrated embodiment; thus the description of features applies to both elements unless expressly described otherwise. The proximal ring 506 is made of a small diameter member, generally a rigid bio-compatible material, e.g. metal, plastic, or the like, that is shaped to form a circle, where the circle generally lies on a common flat plane.

The small diameter member is formed in a circular manner such that the two ends of the member are adjacent each other, resulting in a slight gap between the ends. The proximal ring 506 has a through-hole, establishing an inner diameter that is greater than the outer diameter of the cylindrical body of the flanged sleeve 404. The diameter of the small diameter member is less than the wall thickness of the proximal end of the proximal mount 300. As will be discussed in detail below, the gap between the ends of the member provides access for the sutures 312 connection to the ring and subsequently to the delivery device 316. Alternatively, there is no gap in the ring, creating a continuous circle, whereby the sutures are individually tied onto the rings, or just folded over the ring and press fit into the annular groove, as discussed in further detail below, at the same time as the ring.

With continued reference to FIGS. 5 and 6, an embodiment of the implant 200 includes a plurality of the proximal interface 202 and the distal interface 204, as shown. The proximal interface 202 establishes a connection, or attachment, location for the suture 312 and the distal interface 204 establishes an attachment location for the suture 314. Thus the proximal interface 202 and distal interface 204, in combination with the sutures 312, 314, connect the implant to the delivery device 316. The shape and location of the interfaces 202, 204 can vary according to a physician's particular needs, and their shapes are not required to be identical, although such a configuration is possible. Their shape can be any three-dimensional geometry providing connection capability to the suture 312, e.g. an eyelet as shown, a hook, a radiused or sharp angled triangle element, a block, a sphere, a t-shaped leg, or the like, and any combination thereof. Additionally, the suture contacting surfaces of the interfaces 202, 204 can vary as well, e.g. smooth, grooved, random discontinuous roughness, or the like, and any combination thereof. Alternatively, the interfaces can be located anywhere on the implant instead of at the proximal and distal ends provided sufficient tension on the implant 200 can be achieved to obtain a reduced diametral cross-section of the implant, as discussed in detail below. For example, in one embodiment an intermediate interface 206 is provided just proximal the foreshortening portion. In one such embodiment, proximal sutures connect to the intermediate interface, extend along the non-foreshortening portion and through the proximal interface, and then to the proximal mount 300.

With continued reference to FIG. 5, the illustrated embodiment of the implant 200 has a plurality of anchors 210 for grasping the tissues of the vasculature at a desired location to hold the implant in place, as described in detail above. Alternatively, other embodiments for other uses may not have anchors.

The above described individual details will now be described with respect to their assembled arrangement and configuration to comprise the medical implant system. Distal assembly 112 is assembled to provide handle 102 controlled longitudinal displacement of the pull rod 304 and the nose cone 308. The pull rod and the nose cone are rigidly coupled together and share a substantially common longitudinal axis extending through their respective through-holes, or lumens. The coupling is achieved by way of the external thread 414 on the distal end of the pull rod 304, which threadingly engage the inner surface of the nose cone 308 through-hole, which includes a corresponding internal thread feature adjacent the nose cone proximal end.

With continued reference to FIGS. 3 and 4A, the nose cone 308, prior to being coupled to the pull rod 304, is first coupled to the distal mount 302. The distal mount 304 through-hole is received on the nose cone 308 neck that protrudes proximally. The distal face of the distal mount 304, having the increased cylinder wall thickness, is abutted against the flat surface of the nose cone flange, which is orthogonal to the longitudinal axis of the neck, nose cone and distal mount 304, all of which are substantially co-axial. The distal mount 304 is coupled via friction, where the diameters of the neck and the through-hole are sufficiently closely toleranced that a press fit occurs between the two details.

Alternatively, or additionally, the distal mount 304 may be held in place by a distal collar 406, which is a ring or washer having sufficient thickness to be threaded on the inner surfaces of a through-hole extending along a longitudinal axis. The through-hole is sized to threadingly engage the pull rod 304 external thread 414. Thus, in the illustrated embodiment the distal mount 304 would be threadingly pressed between the distal collar 406 and the nose cone 308 flange as the external threads of the pull rod engage both the nose cone 308 and the distal collar. Alternatively, the distal collar 406 can be frictionally press fit on the distal end of pull rod 304 to abut the proximal face of the distal mount 304. Thus, the distal mount 304 is pressed between the nose cone 308 and the distal collar 406 by press fit friction and thread engagement, either alone or in combination.

In the embodiment shown in FIGS. 3 and 4, the flanged sleeve 404 is configured to secure the proximal mount 300 onto the proximal stop 306. In one sequence, the proximal mount 300 is first inserted onto the flanged sleeve 404, then the flanged sleeve 404 is inserted onto the proximal stop 306. Further details of the insertion steps are such that the through-hole of the proximal mount 300 is sized to fit snugly onto the cylindrical body of the flanged sleeve 404. The proximal mount is initially inserted onto the proximal end of the sleeve 404 and slid distally until the distal face of the proximal mount abuts the radially outward protruding lip 412 of the sleeve 404. The through-hole of the flanged sleeve 404 is sized to fit snugly, via friction of the two mating surfaces, onto the elongate cylinder surface of the proximal stop 306. Alternatively, the proximal mount and the flanged sleeve can be an integral single-piece detail that achieves the described features and functions, eliminating the need for friction between the two details.

The sleeve 404 is then inserted onto the proximal stop 306 distal end and slidingly displaced proximally along the cylinder length toward the support 310. A gap 'A' exists between the proximal face of the proximal mount, where gap 'A', as shown in FIG. 3B, is established by the longer length accorded to the cylinder of the flanged sleeve 404 as compared to the longitudinal length of the proximal mount 300. Therefore, in the illustrated embodiment of FIG. 3B, a proximal mount 300 moved all the way distally against the lip of the sleeve 404 will result in the proximal end of the flanged sleeve 404 creating the gap 'A' between support 310 and mount 300.

The pull rod 304 proximal end is coupled to the distal end of the flexible extension tube 118 of the proximal catheter 116, establishing longitudinal displacement capability and communication between the pull rod 306 and the handle 102. The displacement capability is via the actuator 104, because the flexible extension tube 118 of the proximal catheter 116 proximal end is coupled to the actuator 104, the actuator 104 is located at the distal end of the handle 102, and actuating the actuator pushes the flexible extension tube 118 of the proximal catheter longitudinally. The pull rod 304 proximal end terminates at the coupling to the flexible extension tube 118 of the proximal catheter 116 in the general area adjacent the proximal stop 306 proximal end when the delivery device 316 is assembled. Thus the pull rod 304 and the flexible extension tube 118 of the proximal catheter 116 extend through and slidingly engage within the proximal stop 306, however the pull rod 304 consumes the majority of the longitudinal length within the proximal stop 306 when the stop and the pull rod are in the un-extended longitudinal state, as shown in FIGS.

3A, 3B, and 4A. Such a configuration advantageously establishes a level of stiffness between the proximal mount 300 and the distal mount 302 that are affixed to the proximal stop 306 and the pull rod 304, respectively, the portion of the delivery device that locates and deploys the implant 200. Alternatively, the respective lengths, endpoints and connect locations between the proximal stop 306 and the pull rod 304 can vary such that the coupling does not occur adjacent the proximal stop proximal end, provided sufficient control of the implant 200 is achieved.

In an assembled configuration of the illustrated embodiment of FIGS. 3A and 3B of the delivery device 316, prior to installation of the implant 200, the proximal stop is not free to slide over the coupled flexible extension tube 118 and pull rod 306. The flexible sheath 120, that covers and protects the flexible extension tube 118 and is fixedly attached to the handle 102 at the proximal end of the sheath 120, is abutted and/or coupled to the proximal end of the proximal stop 306 at the opposing distal end of the sheath 120. Thus the proximal stop 306, the proximal mount 300, the flexible sheath 120, and the handle 102 are coupled together, effectively functioning as a single member in the assembled state, with the proximal stop 306 being a stiffer relative portion of the effective member as compared to the flexible sheath 120. All through-holes and inner diameters share substantially coincident longitudinal axes.

Similarly, in the assembled state, the nose cone 308, the distal mount 302, the pull rod 304, and the flexible extension tube 118 are coupled together, also effectively functioning as a single member. Thus, the pull rod 304 is a stiffer relative portion of the effective member as compared to the flexible extension tube 118. All through-holes and inner diameters share substantially coincident longitudinal axes. The effective single member comprising the pull rod 304 is the moving element, that moves relative the static proximal stop 306 effective member. The noted movement is controlled by the actuator 104, by proximally and distally moving the nose cone 308, the distal mount 302, and the pull rod 304 through interaction with the flexible extension tube 118.

The pull rod 304 and its effective member is in longitudinally movable communication with the handle 102, and is located within, and thus moves within, the through-hole inner diameter of the proximal stop 306 and its effective member. The actuator 104 moves the pull rod 304 longitudinally relative the proximal stop 306 and its effective member of the handle 102, the flexible sheath 120, the proximal stop 306, and the proximal mount 300. The pull rod 304 and the proximal stop 306 share the same longitudinal axis, their respective axes being substantially coincident. Thus, the two effective members move relative each other. In the illustrated embodiment, the pull rod 304 extends through the proximal stop 306 and the relative longitudinal motion is between the outer diameter surface of the pull rod 304 and the inner diameter surface of the proximal stop 306.

The increased stiffness of the proximal stop 306 and the pull rod 304 provides structural support to the distal assembly 112 that advantageously provides control during positioning and adjustment of the implant, as well as stability during any relative longitudinal motion between the proximal mount 300 and the distal mount 302.

With reference again to FIG. 1, in the illustrated embodiment, the actuator 104 is coupled to the flexible extension tube 118, and actuation means occurs when the rotating knob 122 is rotated about the axis of the barrel 114, and the lumen 106. The actuation means can be any mechanical or electromechanical method known in the art, e.g. thread engagement, spring and detent, worm drive, or the like. It is understood also that, in other embodiments, the actuator 104 can be configured differently in the controller 102, such as being a trigger or the like.

The above described details are combined and configured to provide a distal assembly 112 that readily positions, and is capable of readily repositioning, a medical implant at a desired location within a patient.

The distal assembly 112 advantageously provides for insertion, deployment and repositioning of the implant 200 without requiring external radial or longitudinal deployment forces that carry the risk of harming the tissue of and adjacent to the desired deployment location.

The stent 200 is temporarily secured by coupling means to the delivery device 316 for the insertion and deployment process, after which, when the implant is located as desired, the stent 200 is then removed from the delivery device 316. The removal, or release of the coupling means, and the diameter of the delivery device allows the delivery device to be backed out of the insertion location safely, without harming the vascular tissue through which it passed to gain access to the desired location.

The delivery device 316 has the implant installed, as illustrated in FIGS. 3, 5, and 6 to establish a distal assembly 112 that is fully prepared for delivery and deployment within the patient's vasculature. The installation of implant 200 utilizes the proximal interface 202, the proximal sutures 312, and the proximal ring 506 on the proximal side of the implant. Similarly, on the distal side of the implant, installation utilizes the distal interface 204, the distal sutures 314, and the distal ring 508. The installation sequence for the proximal and distal ends of the implant 200 are identical, thus the description of the proximal end installation accordingly applies to the distal end of the implant 200.

With particular reference to FIG. 4, the installation of the proximal end of implant 200 entails coupling the plurality of proximal sutures 312 to the proximal interface 202 and the proximal mount 300. The connection to the proximal mount 300 occurs via a loop or a knot tied to the proximal ring 506, after which the proximal ring 506 is placed in the annular groove 602 and the suture is aligned in the guideslot 402 to complete the attachment. The proximal suture 312 may be individually tied by a knot at each of the proximal interface 202 and the proximal mount, or can be looped through both with a single knot tying both ends of the suture together. Variation can exist in where the individual knots are tied after individually looping the suture 312 through the proximal interface 202 and the proximal mount.

Advantageously, a knot can be placed adjacent the proximal mount 300 and the suture 312 simply looped through the proximal interface 202. This allows for a single cut of the suture to be made that releases the implant without leaving suture material attached to the implant, but ensures the suture 312 remains attached to the proximal mount upon removal of the delivery device 316 from the patient's vasculature.

With particular reference to FIG. 3, at least two, and preferably several, proximal sutures are used to couple the proximal end of the implant 200 to the proximal mount 300, sufficiently spaced apart circumferentially about the longitudinal axis of the delivery device 316 such that the implant 200 is substantially centered about the axis. FIG. 3 illustrates the implant installed on the delivery device 316 in a longitudinally unrestrained condition, such that the diameter of the implant is at its self-expanding maximum.

The above described details are combined and configured to provide a distal assembly 112 that readily positions, and is capable of readily repositioning, a medical implant at a desired location within a patient. The insertion and deployment sequence, as illustrated in FIGS. 7A-C and 8A-D, is described below.

Once the implant is attached to the proximal and distal mounts, as shown in FIG. 3A, the actuator 104 is actuated to extend, or displace outwardly from handle 102, the flexible extension tube 118. The outward distal displacement is transmitted from the flexible extension tube 118 to the pull rod 304 and the distal mount 302.

This distal displacement of the distal mount 302 lengthens the delivery device 316 distance between the proximal mount 300 and the distal mount 302 which results in a longitudinal tension on the proximal and distal flexible members 312, 314 and thus, the implant 200. The longitudinal tension applied to implant, as described above, extends the longitudinal length and contracts the diameter of the implant 200 to a compacted state, as shown in FIG. 7A. To minimize the contracted diameter of the implant, preferably the guideslots 402 are smaller than the diameter of the nose cone. This allows the sutures 312, 314 to be stretched in tension parallel to the longitudinal axis, which would result in a diameter of implant that approximates that of the sutures 312, 314.

The distal assembly 112 is then inserted, preferably in a minimally invasive manner, into the patient and the endoscope 108 is optionally inserted through the lumen 106, the flexible extension tube 118, the pull rod 304, and the nose cone 308 to provide visualization assistance during the positioning and deployment procedure. The distal assembly is inserted into the vasculature and directed toward the desired location 702, which is the native annulus of the heart valve as illustrated in FIGS. 7A-B.

Figure 7C:
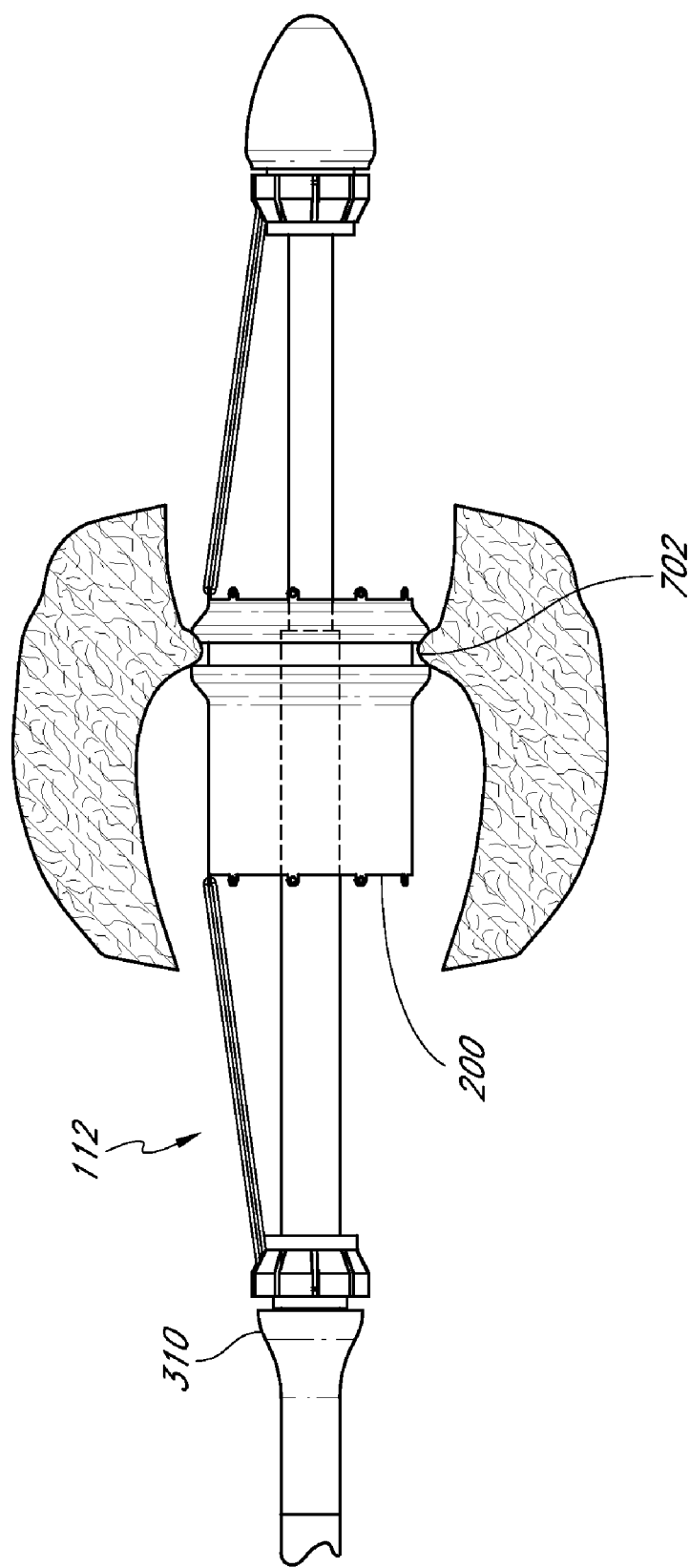

The implant 200 legs 210 are then centered about the desired location 702, as illustrated in FIG. 7B, whereupon the actuator 104 is actuated to retract the flexible extension tube 118, which moves the distal mount 302 proximally toward the handle 102. This longitudinal shortening of the delivery device 316 between the proximal mount 300 and the distal mount 302 allows the longitudinal length of the implant 200 to contract and the diameter of the implant to expand under the self-expanding properties of the implant. Thus, as described above, the foreshortening portion of the implant is contracted and the legs 210 are drawn closer together so as to grasp the heart valve native annulus 702, as illustrated in FIG. 7C.

In a preferred embodiment, after initial deployment the clinician verifies whether the implant has been properly positioned. In one embodiment, position is verified by using the endoscope as discussed above. Should repositioning be desired, the clinician actuates the actuator 104 to extend the distal mount 302 and pull rod 304 such that the implant again extends longitudinally and contracts diametrally, and as a result, disengages from its improperly positioned state.

When the implant 200 is safely disengaged, the deployment process can be repeated after repositioning the implant 200 into an adjusted, desired location 702. The delivery device 316 allows for the above described sequence of position, engage, and disengage, to be repeated until the implant 200 is properly positioned. It is to be understood that while making such adjustments, it may be sufficient to only partially radially contract the implant.

Figure 8A:
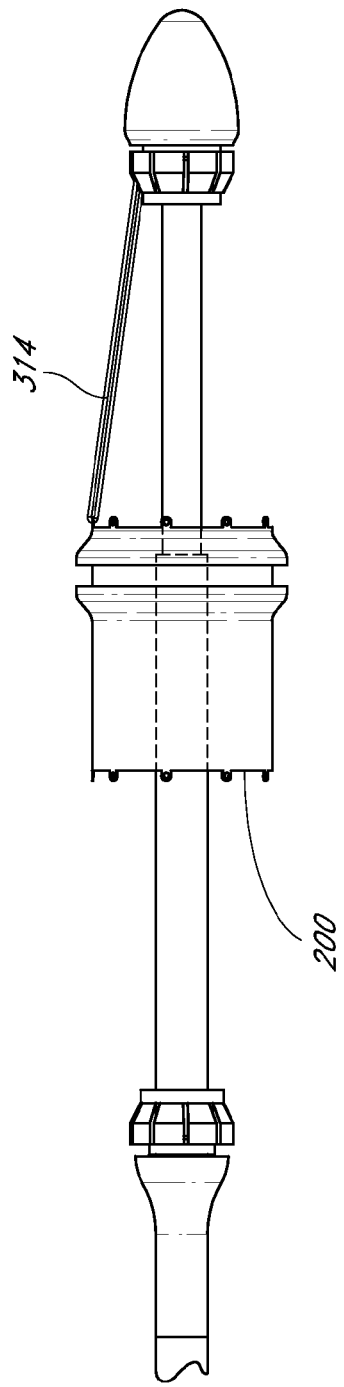
FIGS. 8A-D are side views showing certain stages of operation of the extraction of the delivery device of the medical treatment system of FIG. 1.

With reference to FIGS. 8A-D, after the implant 200 is verified as properly positioned, the delivery device 316 is removed from the implant and the patient's vasculature. The removal sequence is initiated by severing the proximal sutures 312 as described above, leaving the totality of the sutures secured to the proximal mount 300 and ensuring no part of the sutures remain either free within the vasculature or attached to the implant 200 proximal interface 202. In a minimally invasive procedure, preferably the clinician can access, cut, and remove the proximal sutures while the delivery device remains in place. FIG. 8A illustrates the proximal sutures severed, with the proximal sutures not shown for clarity. In another embodiment, the delivery device may have a structure for detaching the sutures from the implant, yet retains the sutures so that they are removed from the patient with the device.

Figure 8B:
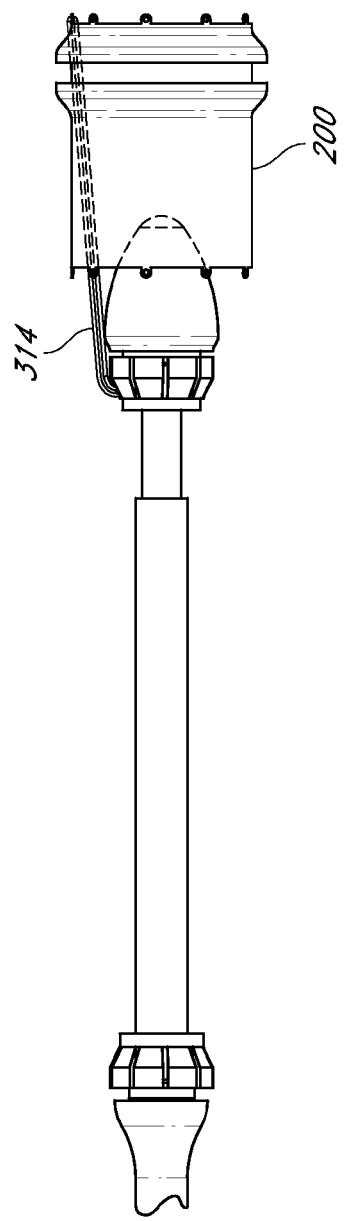

Severing of all the proximal sutures 312 allows partial retraction of the delivery device 316 by actuating the actuator 104 to retract the pull rod 304 in the proximal direction, bringing the distal mount 302 adjacent the proximal stop 300. In combination with the retraction of the pull rod 304, the entire system, except for the implant 200, can be moved proximally to further back the delivery device out of the interior of the implant 200. The delivery device can not be fully removed yet, however, because the distal sutures remain attached to the implant 200. The distal mounts are retracted proximally a sufficient distance relative the implant 200, as illustrated in FIG. 8B, to allow sufficient clearance and access to the distal sutures 314 so they can be cut without necessitating entry of the cutting device into the interior of the implant 200.

Figure 8C:
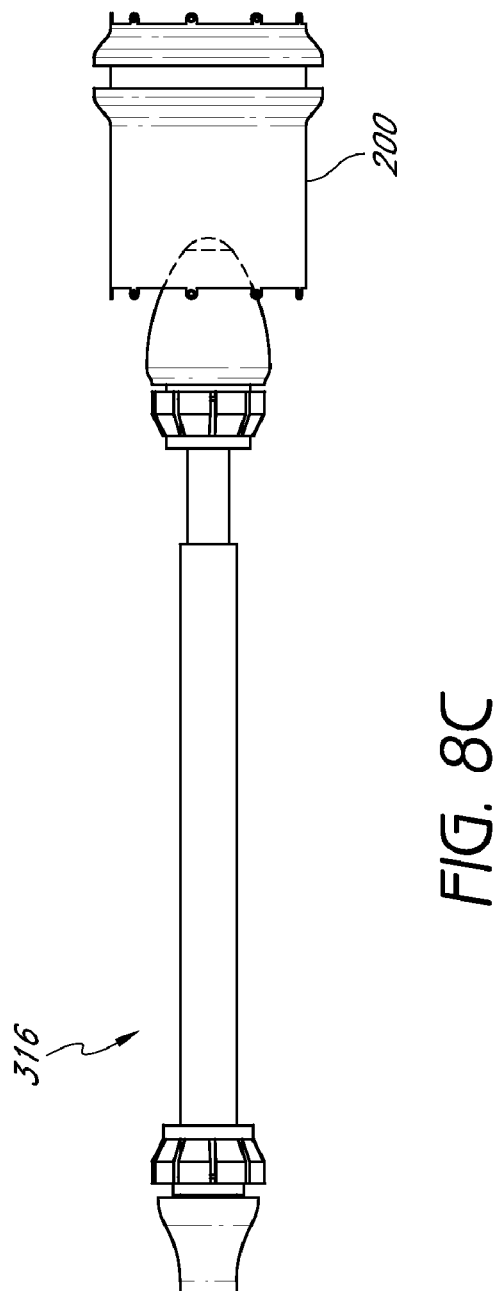
Figure 8D:
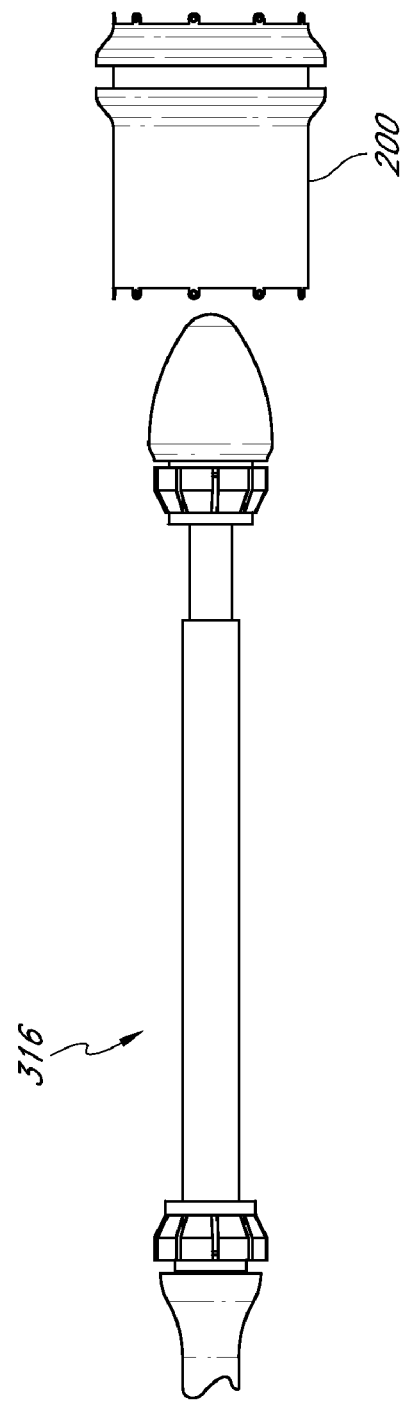

With continued reference to FIGS. 8A-D, such a sequence dictates a preferred sizing of the pull rod 304 whereby the longitudinal length of the pull rod 304 is sufficiently long enough that at full extension two preferred conditions are met. First, that there is sufficient internal overlap between the pull rod 306 and the proximate stop 304 such that adequate stiffness to maintain positioning control of the delivery device exists. Second, that the longitudinal length of the distal suture 314 is approximately at least as long as, and more preferably, 1¼ times as long as, the longitudinal length of the vasculature installed, or unrestrained, implant. The second condition ensures that the distal mount can move to a position so that severing of the distal sutures 314 can be performed without the cutting device entering the implant. Alternatively, the sutures 312, 314 can be configured such that the sutures are disconnected from the implant by other structures and methods, such as the sutures disengaging by other mechanical action from the implant 200, knots being untied rather than severed, or the like. After the distal sutures 314 are severed, the delivery device 316 is free to move as a complete system proximally out of the vasculature and the patient, as illustrated in FIGS. 8C-D.

With reference to FIGS. 9-15, another embodiment of a distal assembly is disclosed. The disclosed embodiment uses spring mechanisms in conjunction with the handle 102 to control the deployment of the implant 200. The spring mechanisms include a proximal spring 918, a distal spring 920, and an intermediate spring 916. The proximal and distal springs 918, 920 are preferably helical compression springs, substantially similar in spring constant, diameter and longitudinal length. Intermediate spring 916 is preferably a helical compression spring, similar in diameter to springs 918, 920 but has a spring constant that is less than that of proximal and distal springs 918, 920, thus requiring less compressive or tensile forces to compress or stretch the spring 920.

The illustrated embodiment further includes a first elongate support member 902 and a second elongate support member 904 that together control the longitudinal motion and displacement of the delivery device during the insertion and deployment of implant 200. The first elongate support member 902, otherwise referred to as a mount tube, is a rigid tube having a distal mount 1002 fixedly attached to the distal end of the mount tube 902. The illustrated embodiment of the second elongate support member 904, otherwise referred to as a pull rod, is a rigid tube in mechanical communication with a controller device such as handle 102 in a similar fashion as described above for distal assembly 112. The pull rod 904 has an outer surface diameter such that the pull rod 904 fits inside of the mount tube 902 and can slidingly engage the mount tube inner diameter.

With reference to FIG. 10, the distal mount 1002, typically integrally or fixedly attached to the distal end of the mount tube 1002, has a generally cylindrical shape that is coincident with the mount tube 902. The distal mount 1002 includes at least one guideslot 1004, which is located on a proximal lip 1006, a groove 1008 that is disposed circumferentially about the distal mount 1002, and a distal lip 1010 located at the distal end of the mount tube 902. The groove 1008 is further established by and located between the proximal lip 1006 and the distal lip 1010. The guideslot 1004 extends longitudinally on the proximal lip 1006.

Figure 9:
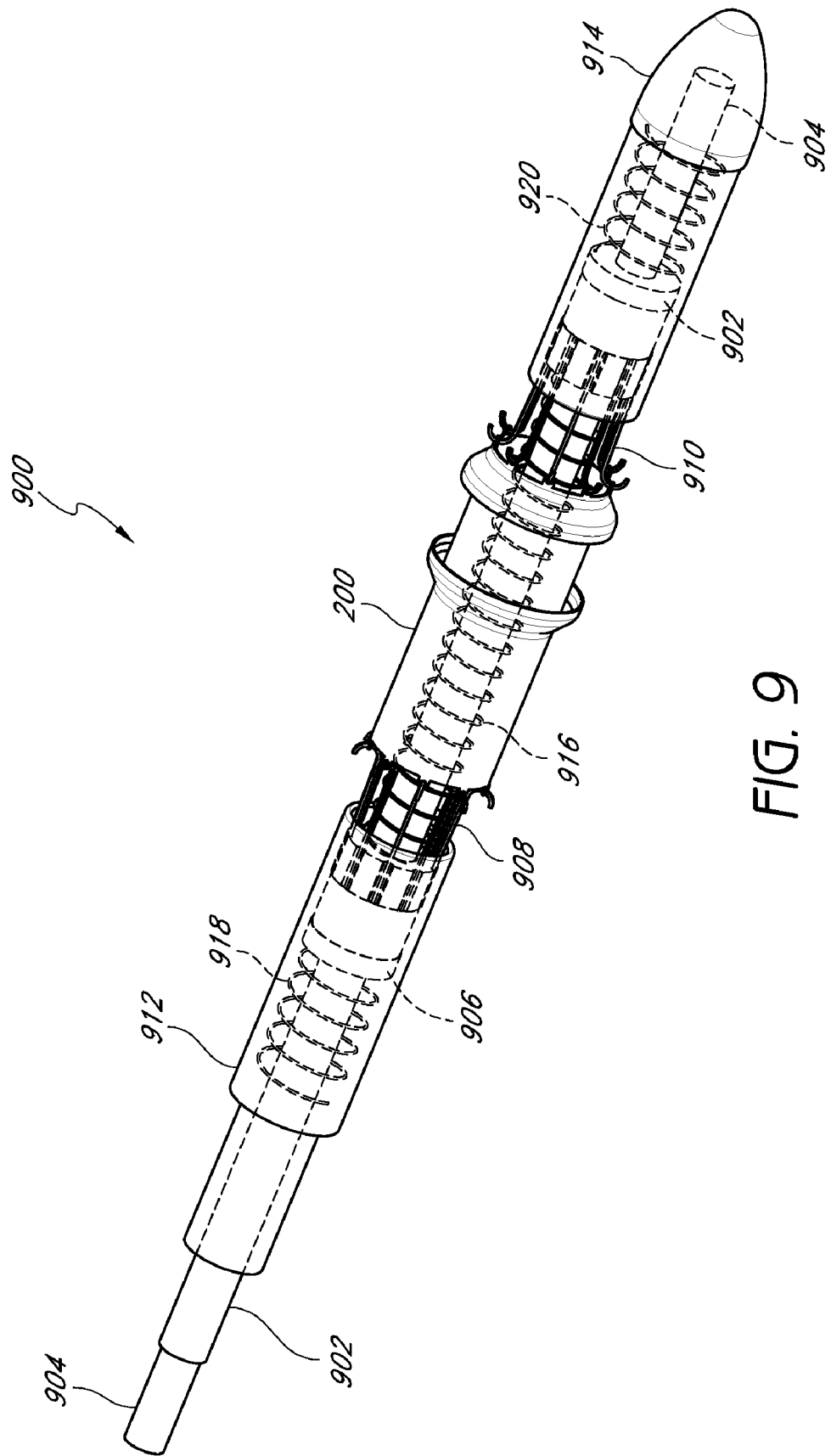
FIG. 9 is a perspective view of another embodiment of a distal assembly of a medical treatment system.

With continued reference to FIGS. 9 and 11, the illustrated embodiment further includes a proximal mount 906, a proximal body 912, a distal body 914, a proximal flexible member 908, and a distal flexible member 910. The proximal mount 906, illustrated in detail in FIG. 11, includes a proximal lip 1104, a groove 1102 that is disposed circumferentially about the proximal mount 906, a distal lip 1106, and at least one guideslot 1108. The proximal mount 906 is configured in a similar arrangement as the distal mount 1002 except the proximal mount 906 includes a through-hole having a longitudinal axis that is sized to slidingly engage the outer surface diameter of the mount tube 902. Additionally, the proximal mount is symmetrically reversed longitudinally relative to the distal mount 1002, such that, for example, the guideslots are located on the distal end of the proximal mount 906.

The proximal flexible member 908, and the distal flexible member 910 are identical, comprised of a flexible member assembly 1200 as illustrated in FIG. 12, but symmetrically opposed on their common longitudinal axis about the implant 200 in the assembled arrangement. The flexible member 1200 includes a plurality of arms 1202, and a ring 1204. The arms 1202 are J-shaped wire-type elements, where the elongate portion is coupled to the ring 1204 and the radiused portion is biased to flare radially outward when the arms 1202 are in an unrestrained condition. The ring 1204 has a longitudinal length and an inner and outer diameter that is configured to mate with the grooves 1102 and 1008 on the respective mounts. The flexible member assembly 1200 preferably is comprised of a semi-rigid, or resiliently flexible material, e.g. metal, plastic, or the like. In alternative embodiments the flexible members can be substantially rigid and still provide the longitudinal tension required as described below.

Figure 14:
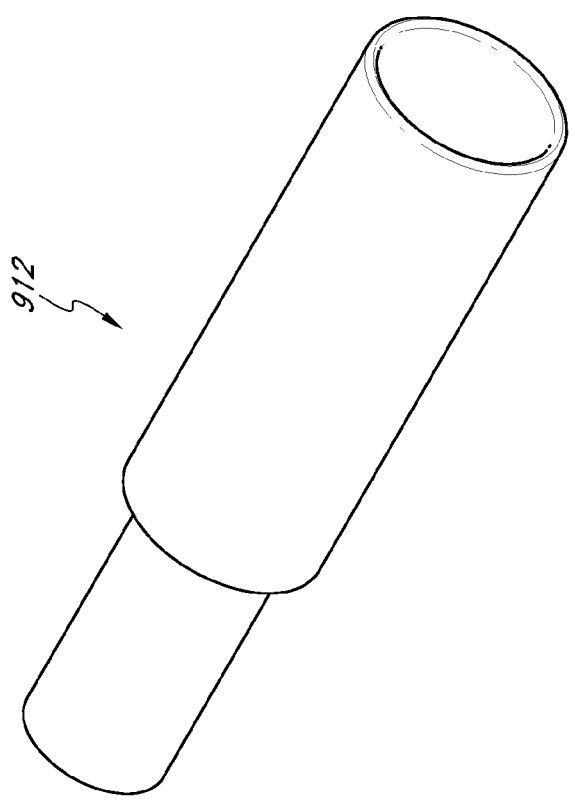
FIG. 14 is a perspective view of a proximal body of the medical treatment system of FIG. 9.
Figure 13:
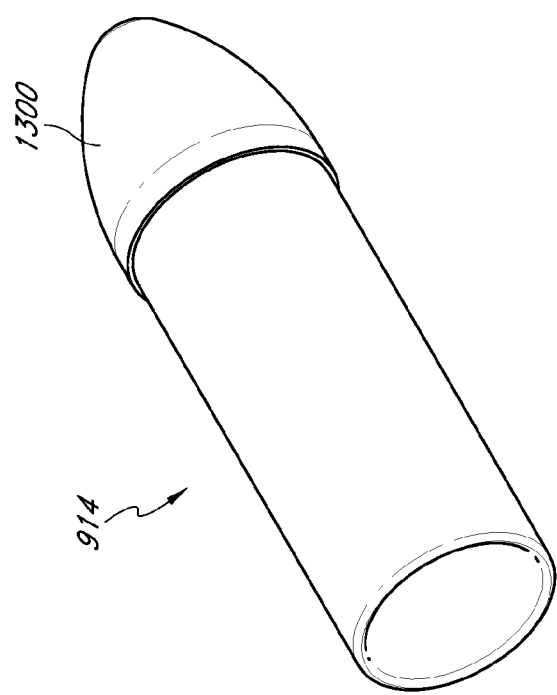
FIG. 13 is a perspective view of a distal body of the medical treatment system of FIG. 9.
Figure 15A:
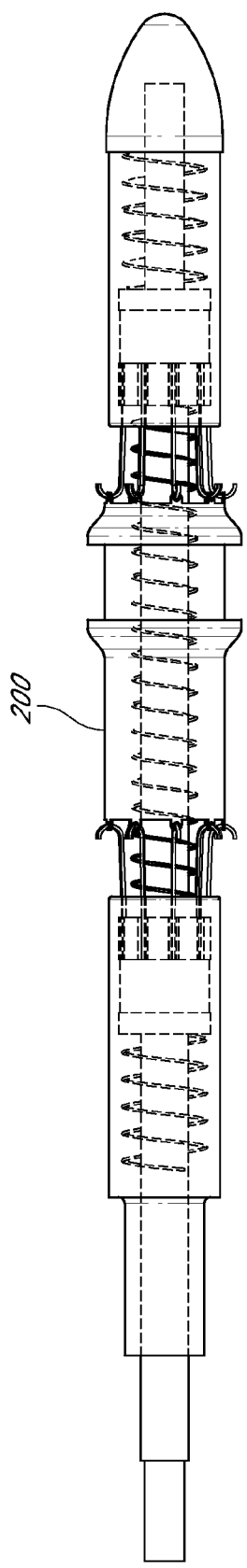
Figure 15B:
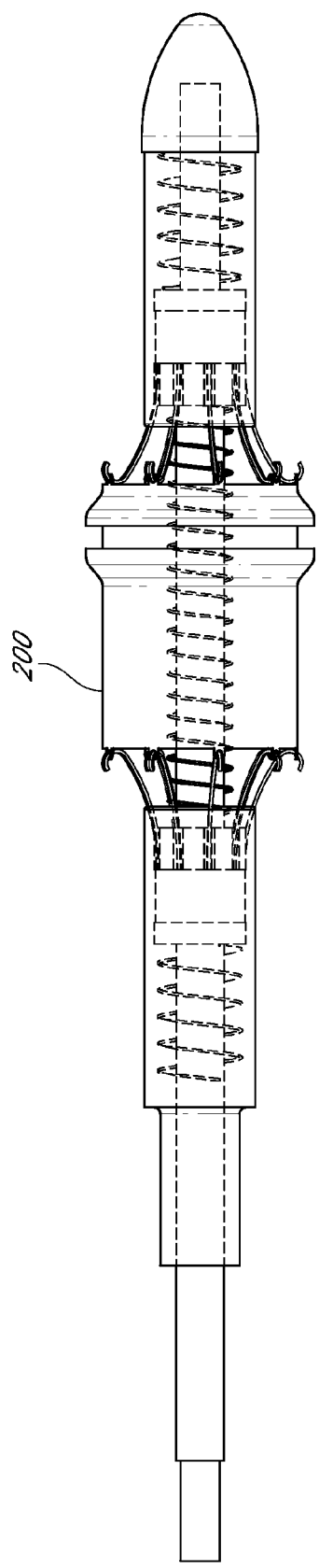
Figure 15E:
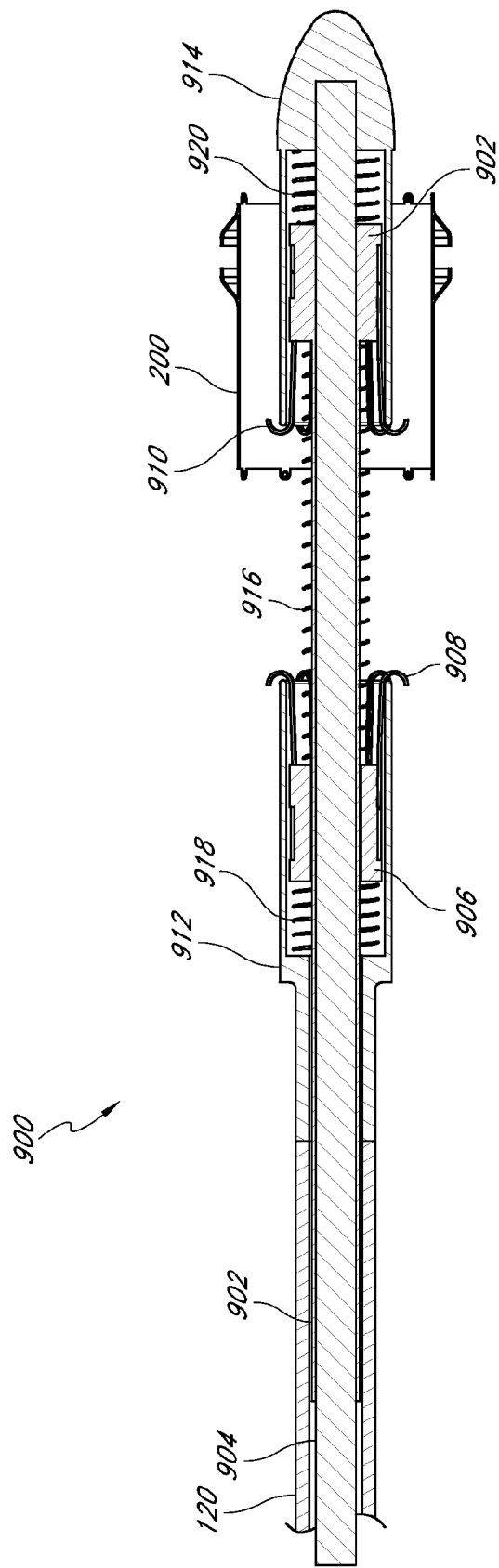
FIG. 15E is a cross-section view of the distal assembly of the medical treatment system of FIG. 9.

The proximal body 912, as illustrated in the embodiment of FIG. 14, includes two cylindrical portions, a smaller diameter cylinder sized to slidingly engage the mount tube 902 and the larger diameter cylinder sized to receive the proximal spring 918 and the proximal mount 906. The distal body 914, as illustrated in FIG. 13 includes a head 1300 having a conical shape similar to the nose cone 308 and a cylindrical body sized and configured to receive the distal spring 920 and the distal mount 1002.

The implant 200 preferably includes proximal and distal interfaces 202, 204 as described above.

The distal end of the pull rod 904 is coupled to the head 1300 of the distal body 914, within the through-hole lumen that is disposed about the longitudinal axis of the head 1300. The distal spring 920 is disposed about the pull rod 904 and located between head 1300 and the distal mount 1002 within the cylindrical portion of the distal body 914.

Prior to coupling the distal body 914 to the pull rod 904 in the illustrated embodiment, the remaining details are assembled on the pull rod 904 as follows. The mount tube 902 has several details installed over the cylindrical tube. Intermediate spring 916 is inserted on the proximal end of the mount tube 902 distally until contacting the proximal end of the distal mount 1002. Next, the distal end of the proximal mount 906 is placed onto the mount tube 902 and the mount 906 is slidingly engaged distally until contacting the proximal end of the intermediate spring 916.

With particular reference to FIG. 9, the proximal spring 918 is then inserted in a like manner, followed by the larger diameter distal end of the proximal body 912. The distal end of the proximal body 912 is inserted on the mount tube 902 until an inner orthogonal flat surface, which transitions the larger cylinder to the smaller cylinder of the body 912, contacts the proximal end of the proximal spring 918. The flexible sheath 120 is then coupled to the proximal end of the proximal body 912, to establish a fixed distance between the proximal body and the controller 102. The proximal and distal mounts 906, 1002 will also have the proximal and distal flexible members 908, 910 installed onto the respective mounts, such that the J-shaped arms are oriented to couple to the implant 200 at the proximal and distal interfaces 202, 204. The distal spring 920 is then placed over the pull rod distal end, and finally the distal body 914 is coupled to the pull rod distal end.

Thus, when the implant 200 is coupled to the proximal and distal flexible members 908, 910 the proximal mount 906 is effectively coupled to the distal mount 1002 via the distal flexible members 908, 910 and the implant 200, with the intermediate spring 916 located between the two mounts 906 and 1002. The intermediate spring 916 urges the mounts longitudinally apart, which supplies tension to retain the implant 200 in a longitudinally extended and diametrally contracted configuration as shown.

With continued reference to FIG. 9, for the distal assembly 900, the flexible sheath 120, not shown, as described above, abuts the proximal end of the proximal body 912. Preferably, and as discussed above, longitudinal displacement of the pull rod 904 due to extraction or contraction via actuating of the actuator 104 occurs within the flexible sheath 120. Thus, the mount tube 902 and the aforementioned installed details on the mount tube 902 essentially float between the nose cone 1300 and the flexible sheath 120. This floating condition allows for operation of the delivery device 900 to insert and deploy the implant 200. The proximal body 912 is prevented from moving toward the handle 102 by the sheath 120.

The implant 200 installation on the delivery device 900 completes the assembly of the distal assembly 900, which is achieved as follows. The intermediate spring 916 is compressed to hold the proximal and distal mounts close enough together to allow the arms 1202 to be coupled to the proximal and distal interfaces 202, 204 of the unrestrained self-expanded implant. Alternatively the implant 200 can be longitudinally extended in tension prior to the coupling to the flexible members to allow the interfaces to complete the coupling, or further still there can be a combination of the two, compression of intermediate spring 916 and longitudinal tensile extension of implant. Once coupled, the intermediate spring is released and allowed to expand, extending the implant longitudinally, as the spring constant is chosen to be sufficient to overcome any resistance in the self-expanding implant to such longitudinal extension.

With reference to FIGS. 15A-E, the method of operation of the distal assembly will be described. More specifically, once the implant 200 is loaded, the delivery device is initially in the compacted state shown in FIG. 15A. The pull rod 904 distal end is coupled to the distal body 914 and the pull rod 904 proximal end is coupled to the actuator 104. The actuator 104 is configured to move the pull rod 904 toward the handle 102 when actuated, so as to pull the distal body 914 toward the handle 102. This relative movement between the distal body 914 and proximal body 912 is resisted by each of the distal spring 920, proximal spring 918, and intermediate spring 916. However, because the intermediate spring 916 has a lower spring constant, the intermediate spring 916 will contract first before either the proximal or distal springs 918, 920.

Contraction of the intermediate spring 916 allows the implant 200 to contract longitudinally and expand diametrally because the mounts 906, 1002 move closer to each other. As the mounts contract and the implant self-expands diametrally, the arms 1202 on the flexible members 906, 910 remain coupled to the implant. Thus, in use, once the distal assembly is properly positioned, the actuator 104 is actuated to begin the longitudinal contraction and engaging of the adjacent surfaces of the desired location 702 as described above, and as depicted in FIG. 15B. In a similar reverse method, the distal assembly can be disengaged and repositioned as discussed above.

Upon successful deployment of the implant 200 the delivery device 900 is next removed from the implant by releasing the arms 1202 and extracting the delivery device. With particular reference next to FIG. 15C, removal occurs by further actuation of the actuator 104 in a manner that moves the pull rod 904 distally away from the handle 102 and concurrently moves the distal body proximally toward the handle 102. The intermediate spring 916 will eventually bottom out in compression and stop contracting. As the actuator continues to move the pull rod 904 proximally, the higher spring constant proximal and distal springs 918, 920, which did not contract previously because the spring constant is higher than the intermediate spring 916, will then contract under the continued compressive forces created by the distal motion of the actuator 104. Preferably, one or more physical stops are disposed on the mount tube 902 to stop further compression of the intermediate spring.

With continued reference to FIG. 15C, as the springs 918, 920 compress, the distal body 914 and the proximal body 912 move toward the implant and the cylindrical bodies adjacent the implant 200 encompass the arms 1202 of the proximal and distal flexible members 908, 910. The motion, combined with movement of the flexible member 908, 910 toward the center of the implant 200, of the cylindrical bodies encompassing the arms 1202 draws the arms radially inward toward the longitudinal axis, to be parallel to the inner diameter surface of the bodies. This motion brings the j-shaped radiused ends of the arms 1202 out of the proximal and distal interfaces 202, 204 of the implant. With additional reference to FIGS. 15D and 15E, the distal assembly is now free to be withdrawn from the interior of the implant and the patient's vasculature system. Notably, the lumen extending through the delivery device 900 is not shown in the cross-section view of FIG. 15E for clarity. In another embodiment, the delivery device includes a detent preventing movement of the pull rod 904 proximally to release the arms 1202. Once the clinician has verified the correct positioning of the implant 200, the detent may be actuated to allow further movement of the pull rod 904.

With reference to FIGS. 16A-B and 17, various embodiments of the handle 102 are shown. FIG. 16A depicts one embodiment of a handle having an actuator 104 driven by rotation of an actuator knob 122. Rotation of the knob 122 engages the flexible extension tube 118 of the proximal catheter 116 so as to longitudinally displace pull rod either proximally or distally, depending on the rotation direction of the knob. The engagement can be applied by various methods, such as rotation of threads or the like. A lever 1600 is optionally included and provides a secondary stop mechanism, such as a detent, that prevents actuation of the flexible extension tube 118 of the proximal catheter unless the lever 1600 is biased against the grip 110, which releases the detent stop mechanism and allows actuation of the proximal catheter.

With further reference to FIG. 16B, a lever and spring loaded embodiment is shown to provide longitudinal displacement capability for the handle 102. The handle 102, as illustrated, includes a lever 1600, and actuator spring 1602, and a locking mechanism 1604. The lever 1600 extends downward from the distal side of the grip 110. This orientation allows a user to hold the grip 110 and concurrently actuate the lever proximally and distally about the connection pivot point that is located at the top of the grip 110 adjacent the barrel 114. The spring 1602 is disposed within the barrel about the outer diameter surface of the lumen 106 and the proximal catheter 116.

With continued reference to FIG. 16B, the proximal end of the spring 1602 is coupled to the top end of the lever 1600 and the distal end of the spring 1602 is coupled to the distal end of the handle 102 or the barrel 114. The spring is located in a compressed configuration, imparting a tensile force on the handle 102 and the lever 1602. The tensile force of the spring 1602 biases the lever in a distal direction about its pivot connection to the handle 102. The locking mechanism 1604 applies a friction force to the flexible extension tube 118 of the proximal catheter 116 preventing longitudinal displacement. In one embodiment, the lever 1600 moves the catheter and the spring 1602 biases the lever 1600 to the closed position, which is away from the grip 110, as shown in FIG. 16B. Actuation occurs when the lever 1600 is pulled toward the grip 110 and the lever pushes the proximal catheter distally, so as to also push the pull rod distally. Lock 1604 then holds the proximal catheter in place. In another embodiment, the sequence can be reversed, such as for the spring driven delivery device 900, such that actuation of the lever 1600 pulls on the flexible extension tube 118 of the proximal catheter to deploy the implant. In one embodiment, the lock 1604 can be configured to actuate a detent that prevents advancement or retraction beyond a specified distance, and the detent can be disengaged upon manipulation of the lock 1604.

With reference to FIG. 17, an alternative embodiment of controller 1700, otherwise referred to as a handle, is shown. The handle 1700 includes a knob 1702, a grip 1704, a dual spring 1708, and an actuator 1706. The knob 1702 is coupled to a longitudinal neck that is further coupled to the flexible extension tube 118 of the proximal catheter 116. The knob 1702 rests in the palm of the user, or physician. The grip 1704 includes at least one radially extending arm that is held by the users fingers. The actuator 1706 extends radially and is actuated by the users thumb. The actuation of the actuator 1706 engages the spring 1708 to selectively lock or allow actuation of the flexible extension tube of the proximal catheter in conjunction with the longitudinal depression of the knob 1702 by the user.

For the embodiments of FIGS. 16A-B and 17, a pump of the lever 1600 or the knob 1702 or rotation of actuator knob 122 allows radial expansion of an associated implant by displacing the flexible extension tube 118 distally or proximally as appropriate. During the deployment and extraction process the proximal and distal mounts 300 and 302 must move toward each other to allow the implant to diametrally expand and subsequently disengage from the implant 200. This is achieved by a plurality of means, both actively and passively. The rotation of knob 122 allows precise control in both longitudinal directions.

Similarly, when the locking mechanism of the actuator 1706 and the locking mechanism 1604 is released, the dual spring will contract and displace the flexible extension tube 118 of the proximal catheter 116 in the proximal direction. An alternative method to the release mechanism is to utilize a detent that will establish a final click lock during the extension of the flexible extension tube 118, and such click with deploy and fix into longitudinal place the flexible extension tube 118. Alternatively a passive mechanism is possible that the mounts are displaced past the point of full expansion and then drop away to disengage freely from the implant 200.

The embodiments discussed above have been discussed in detail in connection with specific designs. It is to be understood, however, that skilled artisans will be able to implement inventive features by employing structures that may differ from the specific structures described above. Applicants in no way intend for the scope of the inventive features discussed herein to be limited to the specific structure used in certain embodiments. For example, although in some illustrated embodiments only the distal-most mount has been actively moved by the user, other embodiments may be made that employ inventive aspects, but which instead actively move only the proximal-most mount, or which actively move both the proximal- and distal-most mounts simultaneously.

In the interest of clarity and consistency of discussion, the illustrated embodiments have been shown in the context of deploying an implant having a particular design. It is to be understood, however, that a variety of implant designs can be employed. For example, the illustrated implant included anchoring legs that would grasp tissue upon foreshortening during radial expansion. Other implant embodiments without anchoring legs can also be used with embodiments employing features discussed herein. Additionally, the illustrated implant has a foreshortening portion and a non-foreshortening portion. It is to be understood that other stent designs having greater- or lesser-sized foreshortening portions can be used, or even stents that have no non-foreshortening portion. Additionally, stents having other configurations of struts, cells and the like can be suitably employed.

In another embodiment, features discussed herein can be combined with other implant delivery apparatus and methods. For example, in one embodiment, in addition to securing the implant under tension as in embodiments discussed above, the implant is also compacted and fit within a sheath, which helps to keep the implant in a small diametral configuration. In one embodiment, the sheath is located on the outer surface diameter of the implant and retains the implant in a diametrally constrained state. In such a configuration, the system holding the implant under tension is a primary restraint system and the sheath is part of a secondary restraint system.

In yet another embodiment, the delivery device may include a secondary restraint structure comprising a line or ribbon extending from a portion of the delivery device and circumferentially encircling the outside of the implant between proximal and distal ends of the implant. At least one end of the line or ribbon can be tightened or let out by the operator manipulating the controller. This secondary restraint works in concert with the proximal and distal mounts to control radial expansion of the implant, and when the proximal and distal mounts are moved toward one another, the clinician can simultaneously let out the ribbon so as to allow the implant to expand. Once the implant is deployed, the ribbon can be retracted into the delivery device and removed from the patient.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure, for example, the flexible members 1200 can be used instead of sutures 312, 314. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A medical treatment system, comprising:
a first elongate support member having a first engagement member;
a second elongate support member having a second engagement member, the second elongate support member being selectively movable relative to the first elongate support member along a longitudinal axis;
a distal mount;
a proximal mount slidingly coupled relative to the distal mount along the longitudinal axis;
a first spring interposed between the proximal and distal mounts so as to bias the proximal and distal mounts longitudinally away from one another;
a self-expanding medical implant that foreshortens upon radially expanding from a radially compacted state;
a distal interface configured to attach the distal mount to the implant;
a proximal interface configured to attach the proximal mount to the implant;
wherein moving the distal mount away from the proximal mount applies a longitudinal tension to the implant causing the implant to expand longitudinally and contract radially and wherein moving the distal mount toward the proximal mount reduces a longitudinal tension in the implant allowing the implant to expand radially toward a fully expanded state;
wherein the first and second engagement members are configured so that as the first and second engagement are moved toward one another, the proximal and distal mounts are urged toward each other and the biasing of the center spring is overcome so that the implant contracts longitudinally and expands radially; and
wherein a second spring is interposed between the second engagement member and one of the proximal and distal mounts, and a third spring is interposed between the first engagement member and the other of the proximal and distal mounts, and the second and third springs each have a spring constant greater than a spring constant of the first spring.

2. The medical treatment system of claim 1, wherein the distal mount is attached to the distal interface by at least one distal flexible member and the proximal mount is attached to the proximal interface by at least one proximal flexible member.

3. The medical treatment system of claim 2, wherein the distal flexible member and the proximal flexible member comprise a suture.

4. The medical treatment system of claim 1, wherein the distal interface comprises at least one distal eyelet and the proximal interface comprises at least one proximal eyelet.

5. The medical treatment system of claim 1 additionally comprising a release mechanism configured to release the distal and proximal mounts from the implant.

6. The medical treatment system of claim 1, wherein the distal interface has a length and the implant has a length in the expanded state, and the distal interface length is at least the same as the implant length.

7. The medical treatment system of claim 1 additionally comprising an endoscope that extends through the first elongate support member so as to provide a view adjacent the distal end of the first elongate support member.

8. The medical treatment system of claim 1, wherein a controller controls the movement of the first elongate support member longitudinally relative the second elongate support member.

9. The medical treatment system of claim 1, wherein an actuator selectively moves the first elongate support member in a longitudinal direction relative to the second elongate support member.

10. The medical treatment system of claim 1 in combination with a secondary restraint system.

11. The medical treatment system of claim 10, wherein the secondary restraint system comprises a sheath configured to hold the implant at least partially therein in a compacted state.

12. The medical treatment system of claim 1, wherein the proximal and distal mounts are arranged between the first and second engagement members.

13. The medical treatment system of claim 1, wherein at least one of the proximal and distal interfaces comprises a ring assembly having at least one flexible arm fixedly attached to the ring at a first end and releasably attached to the implant at a second end, the second end extending beyond the diameter of the ring, and wherein the at least one flexible arm is resilient.

14. The medical treatment system of claim 1, wherein the spring constants of the second and third springs are substantially the same.

* * * * *

UNITED STATES PATENT AND TRADEMARK OFFICE
CERTIFICATE OF CORRECTION

PATENT NO.        : 8,337,541 B2  
APPLICATION NO.   : 12/572180  
DATED             : December 25, 2012  
INVENTOR(S)       : Arshad Quadri and J. Brent Ratz Page 1 of 1

It is certified that error appears in the above-identified patent and that said Letters Patent is hereby corrected as shown below:

In the Claims:

At column 22, line 57, in Claim 1, delete "center spring" and insert -- first spring --, therefor.

Signed and Sealed this
Twenty-fifth Day of June, 2013

Teresa Stanek Rea
*Acting Director of the United States Patent and Trademark Office*